US007895527B2

(12) United States Patent
Zaleski et al.

(10) Patent No.: US 7,895,527 B2
(45) Date of Patent: Feb. 22, 2011

(54) SYSTEMS, USER INTERFACES, AND METHODS FOR PROCESSING MEDICAL DATA

(75) Inventors: John R. Zaleski, West Brandywine, PA (US); Alexander Scarlat, Novi, MI (US); Donald W. Rucker, Philadelphia, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 807 days.

(21) Appl. No.: 11/457,607

(22) Filed: Jul. 14, 2006

(65) Prior Publication Data

US 2009/0055735 A1   Feb. 26, 2009

Related U.S. Application Data

(60) Provisional application No. 60/699,620, filed on Jul. 15, 2005.

(51) Int. Cl.
*G06F 3/048* (2006.01)

(52) U.S. Cl. ................. 715/804; 715/746; 715/781; 715/783; 715/792; 715/803; 702/32; 702/68

(58) Field of Classification Search ............... 600/300, 600/509; 715/740, 771, 781, 792, 746, 783; 715/803, 804, 808; 702/32, 68; 128/188
See application file for complete search history.

(56) References Cited

U.S. PATENT DOCUMENTS

| 5,215,099 | A | * | 6/1993 | Haberl et al. | ............... 600/515 |
| 5,331,549 | A | | 7/1994 | Crawford | |
| 5,684,508 | A | * | 11/1997 | Brilman | ................... 345/440.1 |
| 5,891,049 | A | | 4/1999 | Cyrus | |
| 5,921,920 | A | | 7/1999 | Marshall | |
| 5,966,139 | A | | 10/1999 | Anupam et al. | |

(Continued)

FOREIGN PATENT DOCUMENTS

WO       WO 02/41137 A2    5/2002

(Continued)

OTHER PUBLICATIONS

International Search Report.

*Primary Examiner*—Dennis-Doon Chow
*Assistant Examiner*—Shen Shiau
(74) *Attorney, Agent, or Firm*—Alexander J Burke

(57) ABSTRACT

Illustrative embodiments comprise systems, user interfaces, machine-readable media, and/or methods for automatically acquiring data representing a plurality of different types of medical parameters of a patient, processing the data for presentation to a user via a display device, and initiating display of one or more different image windows, which present processed data representing and corresponding to the plurality of different types of medical parameters of the patient on the display device. Each of the plurality of different image windows is referenced to a single variable scale timeline and is arranged on the display device to permit the user to view values for each of the plurality of different types of medical parameters corresponding to a substantially common time from the single variable scale timeline. A plurality of user interface elements are implemented using object oriented executable code. Each of the plurality of user interface elements are adapted to provide a user with selectable single setting of image display format characteristics shared by the plurality of image windows.

20 Claims, 17 Drawing Sheets

U.S. PATENT DOCUMENTS

| | | |
|---|---|---|
| 6,174,283 B1 * | 1/2001 | Nevo et al. .................. 600/301 |
| 6,224,549 B1 * | 5/2001 | Drongelen ................... 600/300 |
| 6,229,536 B1 * | 5/2001 | Alexander et al. ....... 345/440.1 |
| 6,322,502 B1 | 11/2001 | Schoenberg |
| 6,366,293 B1 | 4/2002 | Hamilton et al. |
| 6,375,614 B1 | 4/2002 | Braun |
| 6,559,868 B2 * | 5/2003 | Alexander et al. .......... 715/781 |
| 6,731,311 B2 | 5/2004 | Bufe |
| 6,875,174 B2 | 4/2005 | Braun |
| 6,876,972 B1 | 4/2005 | Kameda |
| 7,039,878 B2 | 5/2006 | Auer |
| 7,218,325 B1 * | 5/2007 | Buck ....................... 345/440.2 |
| 2002/0054141 A1 * | 5/2002 | Yen et al. .................... 345/804 |
| 2002/0065686 A1 | 5/2002 | Monteleone |
| 2002/0077863 A1 | 6/2002 | Rutledge |
| 2003/0179242 A1 * | 9/2003 | Alexander et al. .......... 345/781 |
| 2004/0002874 A1 | 1/2004 | Shaffer |
| 2004/0054294 A1 * | 3/2004 | Ramseth .................... 600/509 |
| 2004/0077952 A1 | 4/2004 | Rafter et al. |
| 2005/0010117 A1 | 1/2005 | Aguetter |
| 2005/0137653 A1 | 6/2005 | Friedman |
| 2005/0229110 A1 * | 10/2005 | Gegner et al. ............... 715/800 |
| 2006/0080140 A1 * | 4/2006 | Buttner et al. ................ 705/2 |

FOREIGN PATENT DOCUMENTS

| | | |
|---|---|---|
| WO | WO 03/091952 A1 | 11/2003 |
| WO | WO 2004/079554 A1 | 9/2004 |

* cited by examiner

SYSTEMS, USER INTERFACES, AND METHODS FOR PROCESSING MEDICAL DATA

CROSS-REFERENCES TO RELATED APPLICATIONS

This application claims priority to U.S. Provisional Patent Application Ser. No. 60/699,620, filed 15 Jul. 2005.

BACKGROUND

Today, many critical care units employ a paper flow sheet for recording patient medical parameters while a small minority employs a computerized counterpart of it, commonly referred to as an electronic medical record, or EMR. The existing systems, both paper-based and electronic, are inadequate in that, due to their nature and the piecewise manner in which a clinician typically needs to navigate through them, they can cause delay in diagnosis and treatment due to the length of time it takes to process and understand the large amounts of data involved while paging through different views. The interpretation of information is further complicated and the clinician's mental process further fragmented due, in part, to the style differences in the various ways clinicians and allied health professionals record information. These stylistic differences may themselves require interpretation.

Further, typically electronic monitoring (heart rhythm, blood pressure, other pressure tracings), and oximetry are separate from any electronic charting. Existing systems do not have broad controls that can change the configuration of these physiologic parameters concurrently. Exemplary systems, user interfaces, and/or methods address these deficiencies and related problems.

SUMMARY

Illustrative embodiments comprise systems, user interfaces, machine-readable media, and/or methods for automatically acquiring data representing a plurality of different types of medical parameters of a patient, processing the data for presentation to a user via a display device, and initiating display of one or more different image windows, which present processed data representing and corresponding to the plurality of different types of medical parameters of the patient on the display device. Each of the plurality of different image windows is referenced to a single variable scale timeline and is arranged on the display device to permit the user to view values for each of the plurality of different types of medical parameters corresponding to a substantially common time from the single variable scale timeline. A plurality of user interface elements are implemented using object oriented executable code. Each of the plurality of user interface elements are adapted to provide a user with selectable single setting of image display format characteristics shared by the plurality of image windows.

BRIEF DESCRIPTION OF THE DRAWINGS

A wide variety of potential practical and useful embodiments will be more readily understood through the following detailed description of certain exemplary embodiments, with reference to the accompanying exemplary drawings in which.

DEFINITIONS

Figure 1:
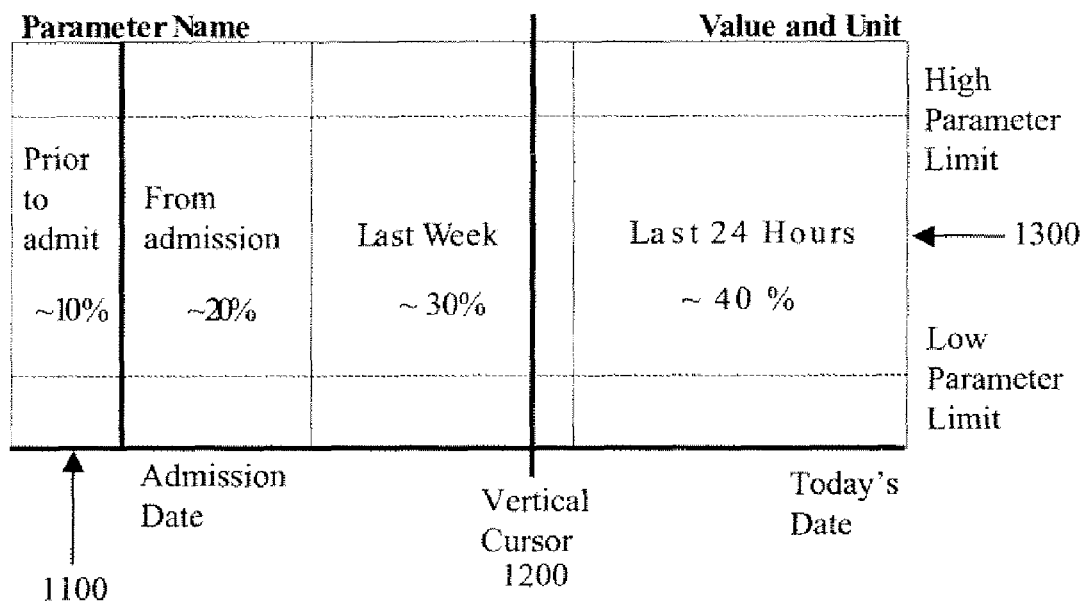
FIG. 1 is an exemplary graphical display component of a chart 1000.

When the following terms are used substantively herein, the accompanying definitions apply. These terms and definitions are presented without prejudice, and, consistent with the application, the right to redefine these terms during the prosecution of this application or any application claiming priority hereto is reserved. For the purpose of interpreting a claim of any patent that claims priority hereto, each definition (or redefined term if an original definition was amended during the prosecution of that patent), functions as a clear and unambiguous disavowal of the subject matter outside of that definition.

a—at least one.

according to—in conformance with.

acquire—to obtain, import, and/or receive.

activity—an action, act, step, and/or process or portion thereof.

adapted for—made suitable, fit, and/or capable of performing a specified function.

adapted to—made suitable, fit, and/or capable of performing a specified function.

amalgamate—to reduce a large set of data elements to a smaller representative set of data elements via a statistical analysis of the large set of data.

and—in conjunction with.

and/or—either in conjunction with or in alternative to.

attribute—a defined property and/or characteristic.

automatically—acting or operating in a manner essentially independent of external influence or control. For example, an automatic light switch can turn on upon "seeing" a person in its view, without the person manually operating the light switch.

can—is capable of, in at least some embodiments.

common—same.

common core attributes—shared defined properties and/or characteristics.

component—a reusable object or program that performs a specific function and is designed to work with other components and applications.

compress—to transform data to a representation that has a reduced number of bytes with respect to the untransformed data.

comprise—include, but not limited to.

comprising—including but not limited to, what follows.

corresponding—related, associated, accompanying, similar in purpose and/or position, conforming in every respect, and/or equivalent and/or agreeing in amount, quantity, magnitude, quality, and/or degree.

cross hair—a pair of mutually orthogonal line segments defining a point of intersection, the point of intersection adapted to be positioned on a target.

data—information represented in a form suitable for processing by an information device.

data point—a discrete data value.

dependent—relying upon and/or contingent upon.

derive—obtain via determining, calculating, and/or looking-up.

device—a machine, manufacture, and/or collection thereof.

differ—to be dissimilar.

display—(v.) to visually render. (n.) a visual representation of something and/or an electronic device that represents information in visual form.

display device—a device for rendering visual information to a user and/or requesting information from the user via a visual rendering. Exemplary display devices comprise a monitor; display; projector; and/or visual indication device, such as a light, flag, and/or beacon, etc.

display processor—a known element comprising electronic circuitry or software or a combination of both for generating display images, image windows, or portions thereof.

documentation tool—a portion of a user interface adapted to receive notes from a user.

element—a component.

entry—data provided via a user interface.

executable application—code or machine readable instruction for implementing predetermined functions including those of an operating system, healthcare information system or other information processing system, for example, in response user command or input.

executable code—machine instructions.

executable procedure—a segment of code (machine readable instruction), sub-routine, or other distinct section of code or portion of an executable application for performing one or more particular processes and may include performing operations on received input parameters (or in response to received input parameters) and providing resultant output parameters.

exponential time scale—a time scale that is based upon values determined via raising an exponential function to a predetermined power.

from—used to indicate a source.

have—to possess as a characteristic, quality, or function.

image—an at least two-dimensional representation of an entity and/or phenomenon.

image display format characteristic—a definable quantity related to rendering a user interface or an element thereof.

image window—a definable portion of a user interface that comprises a defined border.

implement—to accomplish some aim or execute some order.

incorporate—to comprise.

information device—a device on which resides a finite state machine capable of implementing at least a portion of a method, structure, and/or or graphical user interface described herein. An information device can comprise well-known communicatively coupled components, such as one or more network interfaces, one or more processors, one or more memories containing instructions, one or more input/output (I/O) devices, and/or one or more user interfaces (e.g., coupled to an I/O device) via which information can be rendered to implement one or more functions described herein. For example, an information device can be any general purpose and/or special purpose computer, such as a personal computer, video game system (e.g., PlayStation, Nintendo Gameboy, X-Box, etc.), workstation, server, minicomputer, mainframe, supercomputer, computer terminal, laptop, wearable computer, and/or Personal Digital Assistant (PDA), iPod, mobile terminal, Bluetooth device, communicator, "smart" phone (such as a Treo-like device), messaging service (e.g., Blackberry) receiver, pager, facsimile, cellular telephone, a traditional telephone, telephonic device, a programmed microprocessor or microcontroller and/or peripheral integrated circuit elements, a digital signal processor, an ASIC or other integrated circuit, a hardware electronic logic circuit such as a discrete element circuit, and/or a programmable logic device such as a PLD, PLA, FPCA, or PAL, or the like etc.

inherit—to obtain from a previously existing and/or defined entity.

initiate—to begin.

input/output (I/O) device—an input/output (I/O) device of an information device can be any sensory-oriented input and/or output device, such as an audio, visual, haptic, olfactory, and/or taste-oriented device, including, for example, a monitor, display, projector, overhead display, keyboard, keypad, mouse, trackball, joystick, gamepad, wheel, touchpad, touch panel, pointing device, microphone, speaker, video camera, camera, scanner, printer, haptic device, vibrator, tactile simulator, and/or tactile pad, potentially including a port to which an I/O device can be attached or connected.

logarithmic time scale—a time scale that is based upon values determined using a power to which a base, such as 10, must be raised to produce a given number.

machine instructions—directions adapted to cause a machine, such as an information device, to perform one or more particular activities, operations, and/or functions. The directions, which can sometimes form an entity called a "processor", "kernel", "operating system", "program", "application", "utility", "subroutine", "script", "macro", "file", "project", "module", "library", "class", and/or "object", etc., can be embodied as machine code, source code, object code, compiled code, assembled code, interpretable code, and/or executable code, etc., in hardware, firmware, and/or software.

machine-readable medium—a physical structure from which a machine, such as an information device, computer, microprocessor, and/or controller, etc., can obtain and/or store data, information, and/or instructions. Examples include memories, punch cards, and/or optically-readable forms, etc.

may—is allowed and/or permitted to, in at least some embodiments.

medical—of or relating to the study or practice of medicine.

medical parameter—a definable or measurable value related to a patient.

memory device—an apparatus capable of storing analog or digital information, such as instructions and/or data. Examples include a non-volatile memory, volatile memory, Random Access Memory, RAM, Read Only Memory, ROM, flash memory, magnetic media, a hard disk, a floppy disk, a magnetic tape, an optical media, an optical disk, a compact disk, a CD, a digital versatile disk, a DVD, and/or a raid array, etc. The memory device can be coupled to a processor and/or can store instructions adapted to be executed by processor, such as according to an embodiment disclosed herein.

method—a process, procedure and/or collection of related activities for accomplishing something.

network interface—any device, system, or subsystem capable of coupling an information device to a network. For example, a network interface can be a telephone, cellular phone, cellular modem, telephone data modem, fax modem, wireless transceiver, Ethernet card, cable modem, digital subscriber line interface, bridge, hub, router, or other similar device.

number—a quantitative number of items.

object oriented—a group of programming languages and techniques based on the concept of an "object", which is a data structure (abstract data type), encapsulated with a set of routines, called "methods", which operate on the data. Typically, operations on the data can only be performed via these methods, which are common to all objects that are instances of a particular "class". Thus the interface to objects is well defined, and allows the code implementing the methods to be changed so long as the interface remains the same.

panel—an image window.

parameter—a sensed, measured, and/or calculated value.

parent—a node having at least one descendent.

parent class—a category of objects, definable by machine instructions, that are adapted to provide inherited characteristics to one or more child objects created therefrom.

patient—a human or other type of animal under supervision for health care purposes.

patient medical parameter processor—a processor adapted for at least acquiring data representing at least one medical parameter of a patient.

plurality—the state of being plural and/or more than one.

present—to introduce, provide, show, display and/or offer for consideration.

presentation—a process of introducing, providing, showing, displaying, and/or offering for consideration.

process—a series of actions, changes, or functions bringing about a result.

processor—a hardware, firmware, and/or software machine and/or virtual machine comprising a set of machine-readable instructions adaptable to perform a specific task. A processor can utilize mechanical, pneumatic, hydraulic, electrical, magnetic, optical, informational, chemical, and/or biological principles, mechanisms, signals, and/or inputs to perform the task(s). In certain embodiments, a processor can act upon information by manipulating, analyzing, modifying, and/or converting it, transmitting the information for use by an executable procedure and/or an information device, and/or routing the information to an output device. A processor can function as a central processing unit, local controller, remote controller, parallel controller, and/or distributed controller, etc. Unless stated otherwise, the processor can be a general-purpose device, such as a microcontroller and/or a microprocessor, such the Pentium IV series of microprocessor manufactured by the Intel Corporation of Santa Clara, Calif. In certain embodiments, the processor can be dedicated purpose device, such as an Application Specific Integrated Circuit (ASIC) or a Field Programmable Gate Array (FPGA) that has been designed to implement in its hardware and/or firmware at least a part of an embodiment disclosed herein. A processor can reside on and use the capabilities of a controller.

programming object—a grouping of data, executable instructions or a combination of both or an executable procedure.

provide—to furnish, supply, give, and/or make available.

receive—to get as a signal, take, acquire, and/or obtain.

reduce—to make smaller.

render—to make perceptible to a human. For example data, commands, text, graphics, audio, video, animation, and/or hyperlinks. etc can be rendered. Rendering can be via any visual and/or audio means, such as via a display, a monitor, electric paper, an ocular implant, a speaker, and/or a cochlear implant, etc.

represent—to be considered as an acceptable equivalent of.

role—an activity of a person in a particular setting.

said—when used in a system or device claim, an article indicating a subsequent claim term that has been previously introduced.

select—to make a choice or selection from alternatives.

selectable—capable of being chosen and/or selected.

semi-logarithmic time scale—a time scale that is partially based upon values determined using a power to which a base, such as 10, must be raised to produce a given number.

set—to define and/or establish.

share—to have in common.

show—to cause to be seen.

signal—information, such as machine instructions for activities and/or one or more letters, words, characters, symbols, signal flags, visual displays, and/or special sounds, etc. having prearranged meaning, encoded as automatically detectable variations in a physical variable, such as a pneumatic, hydraulic, acoustic, fluidic, mechanical, electrical, magnetic, optical, chemical, and/or biological variable, such as power, energy, pressure, flowrate, viscosity, density, torque, impact, force, voltage, current, resistance, magnetomotive force, magnetic field intensity, magnetic field flux, magnetic flux density, reluctance, permeability, index of refraction, optical wavelength, polarization, reflectance, transmittance, phase shift, concentration, and/or temperature, etc. Depending on the context, a signal and/or the information encoded therein can be synchronous, asynchronous, hard real-time, soft real-time, non-real time, continuously generated, continuously varying, analog, discretely generated, discretely varying quantized, digital, broadcast, multicast, unicast, transmitted, conveyed, received, continuously measured, discretely measured, processed, encoded, encrypted, multiplexed, modulated, spread, de-spread, demodulated, detected, de-multiplexed, decrypted, and/or decoded, etc.

single—existing alone or consisting of one entity.

single variable scale timeline—a temporal axis that comprises a non-linear range.

statistical analysis—to calculate at least one derived value based upon a set of data. Exemplary derived values comprise and/or utilize an average, weighted average, standard deviation, mode, median, curve fitting parameters, probability density function, etc.

substantially—to a great extent or degree.

system—a collection of mechanisms, devices, data, and/or instructions, the collection designed to perform one or more specific functions.

textual notes—user provided alphanumeric characters.

time—a measurement of a point in a nonspatial continuum in which events occur in apparently irreversible succession from the past through the present to the future.

time period—a temporal interval.

time scale—a temporally based chart axis.

together—into a unified arrangement.

use—to put into service.

user—a person, organization, process, device, program, protocol, and/or system that uses a device, system, process, and/or service.

user interface—any device for rendering information to a user and/or requesting information from the user. A user interface comprises one or more display images enabling user interaction with a processor or other device. A user interface includes at least one of textual, graphical, audio, video, animation, and/or haptic elements. A textual element can be provided, for example, by a printer, monitor, display, projector, etc. A graphical element can be provided, for example, via a monitor, display, projector, and/or visual indication device, such as a light, flag, beacon, etc. An audio element can be provided, for example, via a speaker, microphone, and/or other sound generating and/or receiving device. A video element or animation element can be provided, for example, via a monitor, display, projector, and/or other visual device. A haptic element can be provided, for example, via a very low frequency speaker, vibrator, tactile stimulator, tactile pad, simulator, keyboard, keypad, mouse, trackball, joystick, gamepad, wheel, touchpad, touch panel, pointing device, and/or other haptic device, etc. A user interface can include one or more textual elements such as, for example, one or more letters, number, symbols, etc. A user interface can include one or more graphical elements such as, for example, an image, photograph, drawing, icon, window, title bar, panel, sheet, tab, drawer, matrix, table, form, calendar, outline view, frame, dialog box, static text, text box, list, pick list, pop-up list, pull-down list, menu, tool bar, dock, check box, radio button, hyperlink, browser, button, control, palette, preview panel, color wheel, dial, slider, scroll bar, cursor, status bar, stepper, and/or progress indicator, etc. A textual and/or graphical element can be used for selecting, programming, adjusting, changing, specifying, etc. an appearance, background color, background style, border style, border thickness, foreground color, font, font style, font size, alignment, line spacing, indent, maximum data length, validation, query, cursor type, pointer type, autosizing, position, and/or dimension, etc. A user interface can include one or more audio elements such as, for example, a volume control, pitch control, speed control, voice selector, and/or one or more elements for controlling audio play, speed, pause, fast forward, reverse, etc. A user interface can include one or more video elements such as, for example, elements controlling video play, speed, pause, fast forward, reverse, zoom-in, zoom-out, rotate, and/or tilt, etc. A user interface can include one or more animation elements such as, for example, elements controlling animation play, pause, fast forward, reverse, zoom-in, zoom-out, rotate, tilt, color, intensity, speed, frequency, appearance, etc. A user interface can include one or more haptic elements such as, for example, elements utilizing tactile stimulus, force, pressure, vibration motion, displacement, temperature, etc.

value—an assigned or calculated numerical quantity.

via—by way of and/or utilizing.

wherein—in regard to which; and; and/or in addition to.

window—a typically rectangular area rendered on a display device, the area displaying, for example, messages, commands, controls, links, metadata, and/or data, etc., the area displayed independently of other areas rendered on the display device. In various embodiments, windows are resizeable, closeable, reducible in size, hideable, stackable, tileable, and/or scrollable, etc.

DETAILED DESCRIPTION

Exemplary systems, user interfaces, and/or methods provide an object oriented environment that controls concurrent display of multiple different patient parameters. A modular patient telemetry and critical care system architecture comprises a core container object class onto which child classes are overlaid or assembled. These overlaid object classes inherit the base attributes and operations of the parent container class and may be any of a number of numerical or graphical display varieties. These child classes provide instances of specific connectivity to physiologic monitors, other point of care devices, flow sheets for recording of information about the patient, medication administration, intake and output of fluids, physician order entry, and/or other custom display classes that may be created by the user. The displays are "built-up" on top of a parent container class, thus providing an adaptable display (i.e., plug and play) component architecture, the basis of which is a system of object-oriented component models, for example.

Critical care environments produce large quantities of data. The data are usually accumulated from the various biosensors to which a patient is connected. Certain illustrative system-ns, user interfaces, and/or methods address:

A need for an inclusive and concurrent view of patient information, including patient vital signs, monitored information, laboratory, respiratory and interventions within a single and clinically-optimized view presented to the clinician without requiring individual manual selection of each parameter by the clinician, yet allowing concurrent control of parameters by shared interface tools, such that:

Monitored values obtained from a patient, by themselves, might have little meaning and importance in overall diagnosis and treatment. Trends over time might be more important than the monitored values viewed In relative isolation (e.g. is the temperature increasing or decreasing, and how rapidly? is the blood pressure stable or unstable?).

Co-display of dependent and clinically relevant information within the eye span of the clinician is usable for diagnosis and early intervention. The titration of drugs and fluids and the patient's response as detailed in the patient's vital signs to these therapeutic modalities are presented to the user in a concise, coherent, and cohesive way, This is achieved effectively using individual displays linked in an object-oriented fashion: that is, they share common core attributes, inherit attributes and functionality from parent classes. Thus, the individual displays can reflect changes in timeline, compression, and selection concurrently.

In order to gain a rapid and correct understanding of the patient situation, the clinician needs to process large quantities of discrete data points. This function becomes increasingly difficult as the number of medical devices and the amount of data produced by point-of-care medical devices continues to increase.

Certain illustrative systems, user interfaces, and/or methods:

Temporally interconnect physiological graphs, medical devices, therapeutic measures (such as drugs and fluids) and laboratory values into one time line via an object-oriented collection of classes that both inherit base functionality from a parent container class while adding functionality associated with specific child functions. Thus, child classes take on either graphical, numerical, or control display forms, and are defined physically as panels within the overall integrated display.

Allow the viewing of numerical and graphical content at any time interval via a "cross hair" that shows the current value of available panels, regardless of particular parameter. Thus providing a "cross-sectional" view of the patient, from physiology to vitals to medications without requiring redundant selection of these or other panels within the display.

Propagate changes in resolution and/or limits of the time line to panels involved by linking public methods for contracting and expanding timelines across multiple objects, so that a change in the parameter values made using one public method is shared by an object on the a tab and/or panel. As each panel is selected it retrieves anew the parameters values associated with time contraction/dilation (corresponding to resolution) and renders the updated view within that panel's user interface. Data that are older than some specified time frame are compressed to provide general information (visually) as to the nature of the data but within a discrete time scale that spans, for the same physical width in screen, a longer period of time. Thus, a clinician can receive a view of the patient at present, in the near past, and in the historical or long past, all within the same screen display without manipulating the window environment.

Provide up to 4 parameters in a panel, up to 8 panels per page, one page per screen display, and any number of pages per patient for a user to toggle between.

Allow for a profile-driven approach for display, in which objects inherit different characteristics (that is, provide different displays) based upon the role of the user and the user's information needs. Each panel (that is, object class) provides the capability to "know" the user via a profile that is inherited from the top container class and is applied to each child class.

Provide control to any text documentation tools such as physician or nurse notes. The same temporal controls that concurrently control the other display panels are used to select temporally based views for any documentation.

The resulting single integrated display combines a component-wise display architecture with object-oriented software both for documentation and controlling components allowing for common scaling in time and timeline synchronization, historical compression, and standard user interface technology to control in aggregate the view and attributes of numeric data. The display provides for viewing of continuous temporal information presented for any physiological data acquired from patient monitors. The object-oriented architecture allows the user to concurrently control specific display components allowing practical redraw of the display to answer various clinical questions (e.g. show the pulse oximetry, capnography, and monitored patient data over the last 15 hours). These parameters are synchronized in time so that adjusting, compressing, expanding, or otherwise changing the time scale of any one parameter automatically propagates those changes to any other concurrently displayed parameter objects within the user interface. The system allows these changes to be concurrently displayed on the screen in parallel allowing individual parameters to share the same x-axis of time An illustrative control capability provides for the remote control, adjustment, and/or configuration of medical devices through the same user interface, via child panels added in the same manner as the other display panels, and inheriting parent characteristics from the base container. The modular nature allows an individual component to respond uniquely but concurrently to requests for real-time redisplay. This integrated control allows coordination and sharing of longer term maintenance, updating and/or versioning control, and/or simultaneous intermediate redisplay when a patient moves to a new site such as an operating room or recovery room.

Summary statistics, medications, physiology, therapy, and/or key indicators (inclusive of probability density and cumulative density functions) are thus visible to the clinician, enabling automatic updating "best display" architecture in a single integrated display.

The system allows the continuous and concurrent display and control of some or all of the following components, for example, within the span of a single screen (or single group of screens per patient). The use of an object-oriented approach in which panels are employed as overlays on the base container class enables data to be displayed in a clinically optimized way (that is, objects are displayed on top of the panel container in a manner most useful to a particular clinician) in which key parameters are linked and functions are inherited across panels, thus accelerating analysis on clinically relevant information. The method for achieving this capability comprises: the concept of a user interface "widget" or object that is placed hierarchically on top of another pane (specifically, a container). This object carries with it a class structure, including a "shape" and image attribute that defines its appearance and/or properties. The object attributes are inherited from the container class on which the object attributes are placed by linking the physical placement to a series of accessor functions that cause protected parameters of the container class to be shared downwards to the object. In this way each object obtains the "view" of the parameters from the parent. This process draws upon the basic object-oriented inheritance process from parent to child to grandchild. Clinically relevant information comprises:

timeLine;
vital signs;
drugs (both drip and non-drip based medications);
fluids;
totals;
events;
diagnostic results;
therapeutic events; and/or
documentation such as notes, assessments and scoring results;
etc.

This in turn allows medical staff in a critical care environment to rapidly assess the patient situation and thus provide better health care.

The system employs software components encapsulated (implemented) as objects to facilitate synchronization of image window displays and user control of the image window displays. This is achieved via the use of synchronized threads which update the displays periodically, and their synchronization ensures that updates occur upon the completion of specific calculations or receipt of specific data, so that individual views are not "aged" or displaying stale data. The system provides heterogeneous concurrent environments wrapped as objects (not just data streams) and controlled by one environment. The environment variables are maintained by the container objects and are the core from which all other objects are derived or inherited. Thereby ensuring that a single environment is reflected within the object hierarchy. The system provides a dynamic ability to control a set of display parameters and to use object oriented architecture to rescale and reformat displays (e.g. using a differential time compression time scale) as well as the ability to change cursor displays, Time differential compression enables the user to view a broader range of newer data while compressing the older data (in time) so that general trends can be viewed without requiring the user to view the details of the data. This is accomplished by taking a log or semi-log calculated scale in time and rendering the time axis as an equivalent dilated pixel display.

An object-based view provides for display of potentially all clinically-relevant information, including:
- medications and/or fluids input and/or output;
- monitored patient data;
- lab test results;
- device control parameters, and/or
- notes;
- etc.

Plotting timeline selections through the use of cross hairs is automatically reflected in other time related objects (e.g.: if the limits on the display are from current time and four hours back, and the user asks for a change to a 24 hours back limit—then objects on the screen, that are connected to the TimeLine window change limits accordingly.

Linkage of panels and subcomponents joined or added to panels is automatically accomplished through object inheritance. Object inheritance follows the standard object-oriented definition in which child objects inherit parental public and protected classes. As objects are placed on a container, a trigger is initiated to update all inherited object values via accessor functions.

Figure 16:
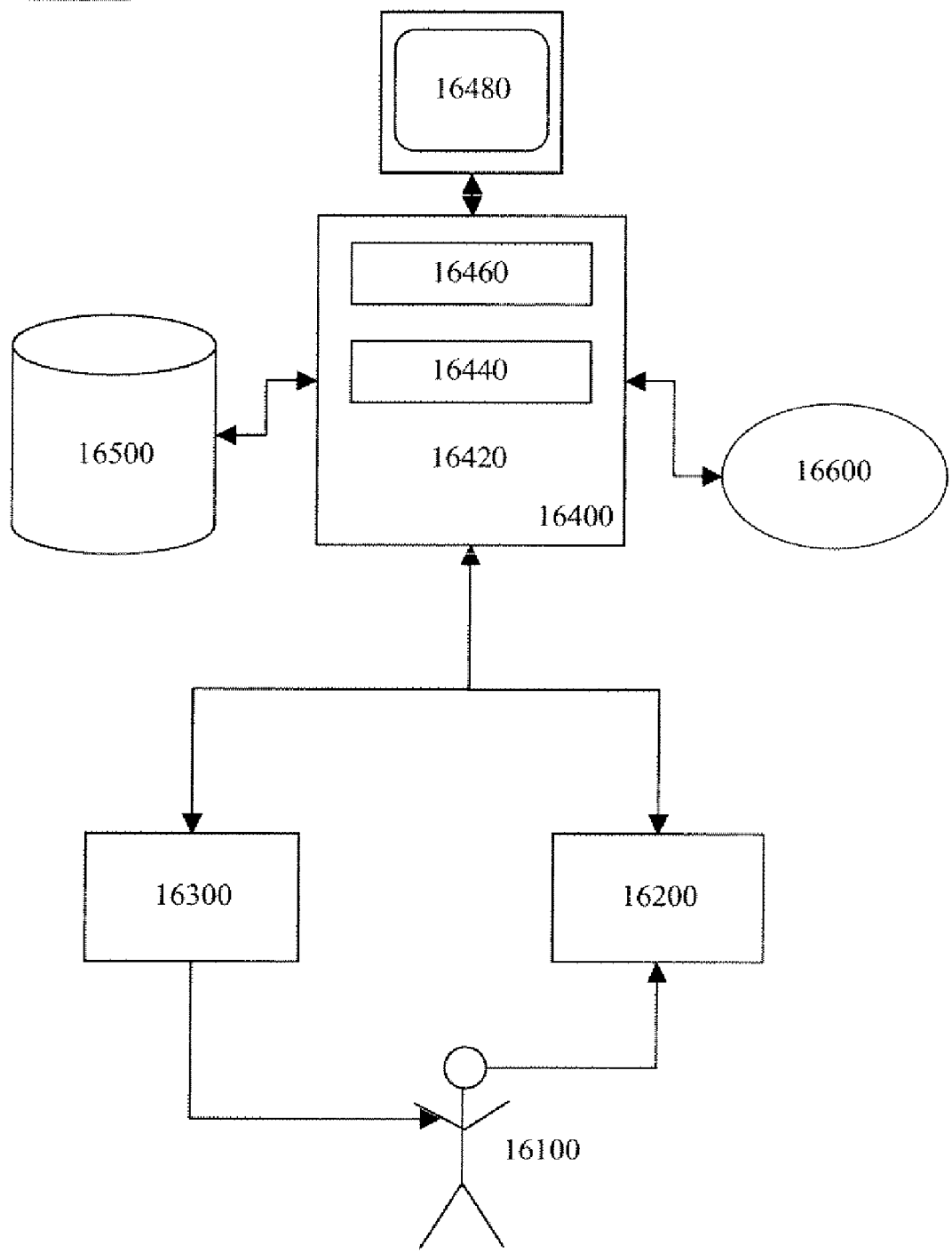
FIG. 16 is a block diagram of an exemplary embodiment of a system 16000.

FIG. 16 is a block diagram of an exemplary embodiment of a system 16000. Patient 16100 is monitorable via a sensor 16200. Sensor 16200 might be a thermometer, sphygmomanometer, electrocardiogram, blood chemistry monitor, respiratory monitor, and/or pulse monitor, etc. Sensor 16200 is adapted to provide a discrete and/or continuous measurement signal to an information device 16400. System 16000 comprises a medicament dispensing device 16300. Medicament dispensing device 16300 dispense medicaments such as an antibiotic, anti-inflammatory, coagulant, anti-coagulant, analgesic, hormone, insulin, and/or sleeping inducing medicament, etc.

Information device 16400 is adapted to transmit instructions to medicament dispensing device 16300. Information device 16400 comprises a user program 16420 and a user interface 16-480. User program 16420 is adapted to provide a user with temporal information related to monitored values of patient 16100 obtained and/or derived from sensor 16200. User interface 16480 is adapted to receive information and/or notes from the user related to the care of patient 16100. User interface 16480 is adapted to provide graphically displayed information relative to the care of patient 16100. Information device 16400 is coupled to a memory device 16500 and/or a network 16600.

Information device 16400 comprises a patient medical parameter processor 16440, which is adapted for automatically acquiring data representing one or more medical parameters of a patient and processing the data for presentation to a user via a display device, such as user interface 16480. Information device 16400 comprises a display processor 16460, which is adapted for initiating display of one or more image windows presenting processed data representing the one or more medical parameters of the patient. The one or more image windows are derived using a corresponding plurality of object-oriented programming objects sharing common core attributes and inheriting attributes from parent classes.

The one or more windows, displayable via user interface 16480, incorporate a single variable scale timeline. The single variable scale timeline includes a first time period having a first time scale and a second time period having a second time scale, the first time scale differing from the second time scale. The first time scale is presented together with data representing compressed medical parameter data of the patient. Alternatively, the single variable scale timeline can comprise a single non-linear time scale, such as a logarithmic, semi-logarithmic, and/or exponential, time scale, with non-compressed medical parameter data displayed along a first predetermined portion of the time scale and compressed medical parameter data displayed along a second predetermined portion of the time scale.

The compressed medical parameter data comprises a reduced number of data points. The reduced number of data points is derived using statistical processing to amalgamate data points. For example, a set of data points taken every second over a two-hour period could result in 7200 data points. That set might be averaged, and a single data point generated for use in a display in lieu of the 7200 data points. As another example, the 7200 data point set might be modeled via a curve-fitting algorithm. An equation derived from the curve-fitting algorithm might be utilized to obtain a subset of derived points, such as six points, that can be used in the display. The one or more user interface elements comprise a cross hair adapted to show values for each of the one or more medical parameters of the patient. Each of the values corresponds to a substantially common time from the single variable scale timeline and/or single non-linear time scale.

Display processor 16460 is adapted for initiating a display of one or more user interface elements implemented using object oriented executable code. The one or more user interface elements comprise a documentation tool adapted to receive entry of at least textual notes. The one or more user interface elements are dependent on a role of the user. For example, user interface elements for a physician might be different from user interface elements for a registered nurse. Each of the one or more user interface elements is adapted to provide a user selectable single setting of image display format characteristics, such as a time range, time value, and/or time scale, etc., shared by the one or more image windows.

Figure 17:
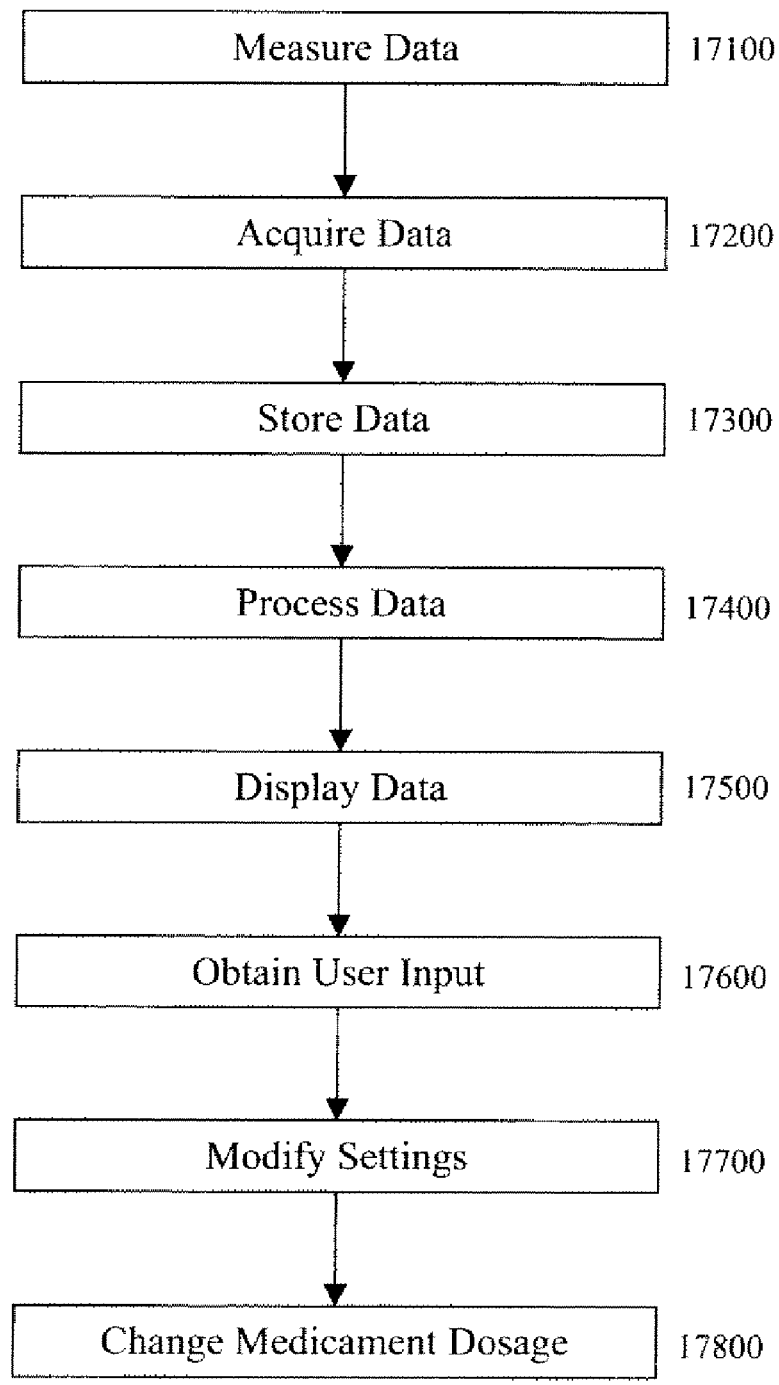
FIG. 17 is a flowchart of an exemplary embodiment of a method 17000.

FIG. 17 is a flowchart of an exemplary embodiment of a method 17000. At activity 17100, patient data is measured. The data are measured by one or more sensors and are transmitted via a wired and/or wireless medium to an information device.

At activity 17200, patient data are acquired. The data are acquired manually and/or automatically and represent one or more medical parameters of a patient. The data are acquired by the information device.

At activity 17300, patient data are stored. The data are stored in a memory device associated with the information device. The data are available to be retrieved by the information device and/or any other information device communicatively coupled thereto.

At activity 17400, patient data are processed, such as via a patient medical parameter processor. For example, the patient data are statistically analyzed, amalgamated, compressed, condensed, charted, and/or graphed, etc. The data are prepared for display by a display processor adapted for automatically processing the data for presentation to the user. The data are rendered to a user via a display device that displays one or more image windows comprising one or more panels.

At activity 17500, patient data is displayed. A display is initiated of one or more image windows presenting processed data representing the one or more medical parameters of the patient. The one or more windows incorporate a single variable scale timeline. The single variable scale timeline comprises a first time period having a first time scale and a second time period having a second time scale. The first time scale differs from the second time scale. The first time scale is presented together with data representing compressed medical parameter data of the patient. Alternatively, the single variable scale timeline can comprise a single non-linear time scale, such as a logarithmic, semi-logarithmic, and/or exponential, time scale, with non-compressed medical parameter data displayed along a first predetermined portion of the time scale and compressed medical parameter data displayed along a second predetermined portion of the time scale.

The compressed medical parameter data comprises a reduced number of data points as compared to uncompressed medical parameter data. The reduced number of data points is derived using statistical processing to amalgamate data points.

A display is initiated, the display comprising one or more user interface elements implemented using object oriented executable code. Each of the one or more user interface elements is adapted to provide a user selectable single setting of image display format characteristics, such as a time range, time value, and/or time scale, etc., shared by the one or more image windows. The one or more image windows are derived using a corresponding plurality of object-oriented programming objects that share common core attributes and inherit attributes from parent classes. The one or more user interface elements comprise a cross hair adapted to show values for each of the one or more medical parameters of the patient. Each of the values corresponds to a substantially common time from the single variable scale timeline. The one or more user interface elements comprise a documentation tool adapted to receive entry of at least textual notes from the user. The one or more user interface elements are dependent on a role of the user. Thus, a physician is provided with a display that is distinct from a display provided to a nurse practitioner.

At activity 17600, a user input is obtained, The user input is adapted for modifying the display and/or a treatment regimen associated with the patient. For example, the user input might adjust a time scale and/or a set of data displayed via the display device.

At activity 17700, patient settings are modified. For example, a user might desire to change a patient status and/or a sensing or medicament device connected to the patient. As another example, a time associated with patient monitor trend displays might be modified responsive to a manual or automatic determination that a predetermined threshold and/or a predetermined rate of change have been exceeded, As a further example, an event such as a medicament change might be used to generate a time of demarcation between data obtained prior to the medicament change and data obtained thereafter. Thereby, an automatic statistical analysis is usable to determine effects in sensed data occurring as a result of the medicament change.

At activity 17800, a medicament dosage is changed. The medicament dosage is changed responsive to information displayed to the user via the display device. For example, the information device might automatically determine and/or recommend a change in a medicament dosage responsive to a measurement and/or a measurement trend. As another example, the user changes the medicament. The display is updated and/or automatically changed as a result of a detected change in the medicament.

Particular operative embodiments are illustrated in FIGS. 2-14. Each of FIGS. 2-14 are intended to be illustrative and not limiting regarding claimed subject matter or other potential embodiments. Exemplary plots provide a structural representation of data, including minimum and maximum parameter values, parameter name, and time axis, such as shown graphically in FIG. 1.

Exemplary embodiments are based upon a container class and child container class structure. For example, the exemplary window illustrated in FIG. 12 was developed via the container class and child container class structure. The container classes and child container classes are built up in accordance with FIGS. 2-14.

Changes in the plots and/or panels occur as changes occur in received data. For instance, showing a ventilator panel (i.e., image window) within the user interface after extubation just wastes real estate in the user interface. After extubation takes place, the system detects the change in the status of the patient. The system then archives results obtained prior to extubation, and removes the panel for the ventilator from the user interface.

An individual panel (component) can also have individually controlled features. The system is adapted to automatically display information about new patient monitoring components as hardware is added. In addition, on "plugging in" a new patient monitoring device, the system automatically requests and/or receives one or more current parameterized control settings. The received control settings are then automatically transferred to a displayed panel.

FIG. 1 is an exemplary graphical display component of a chart 1000, which illustrates multiple data compression modes, current data, and parameter high and low values. The figure approximates a logarithmic compression interval in which newer data are rendered over approximately half the chart. The linear timeline is scaled to a logarithmic scale, and then rendered in the equivalent pixel map within the user interface.

Chart 1000 comprises an abscissa 1100, which charts data regarding a patient over a predetermined time period. The patient data is rendered beginning at a time prior to admission to a medical facility and continues from a time of admission until a present time. A scale of abscissa 1100 is non linear, with more data points per hour displayed during a past 24 hours as compared to data points displayed from prior days. For example, abscissa 1100 can be divided at a cross-hair 1200. Information left of cross-hair 1200 is approximately linear, but displays compressed data from a first predetermined time period. Information to the right of vertical cursor 1200 is linear over a shorter time period and is scaled differently in time from a portion of chart 1000 left of vertical cursor 1200. Chart 1000 indicates a name of a displayed parameter and a value of the displayed parameter. Chart 1000 comprises an ordinate axis 1300, which represents a value of the displayed parameter. Chart 1000 comprises a high limit and a low limit, either of which can be indicative of a medical condition for which intervention is desired.

Figure 2:
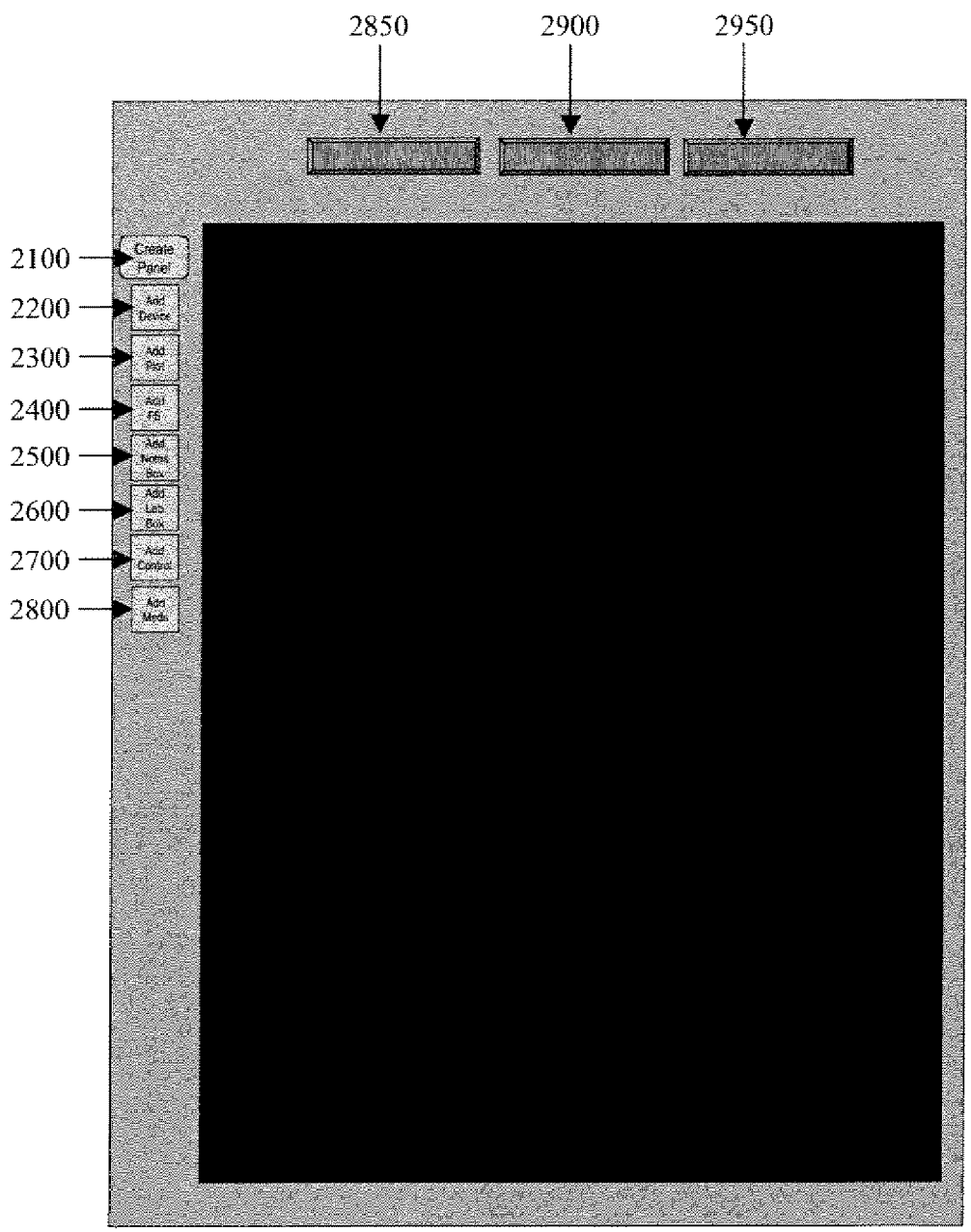
FIG. 2 is an exemplary user interface element adapted to define a base container class.

FIG. 2 is an exemplary user interface element adapted to define a base container class. Child classes are placed on this class. As they are placed, they inherit specific attributes and functionality from the base container class (also known as "parent" class).

The specific types of component features that are supported by and benefit from the plasticity of the interface include icons, such as:
  Create panel icon 2100
  Add device icon 2200;
  Add plot icon 2300
  Add flowsheet icon 2400;
  Add lab icon 2500;
  Add notes, assessments icon 2600;
  Add meds icon 2700;

Add control icon 2800
User roles icon 2850;
Select user profile icon 2900; and/or
Manage users icon 2950, etc.

Figure 13:
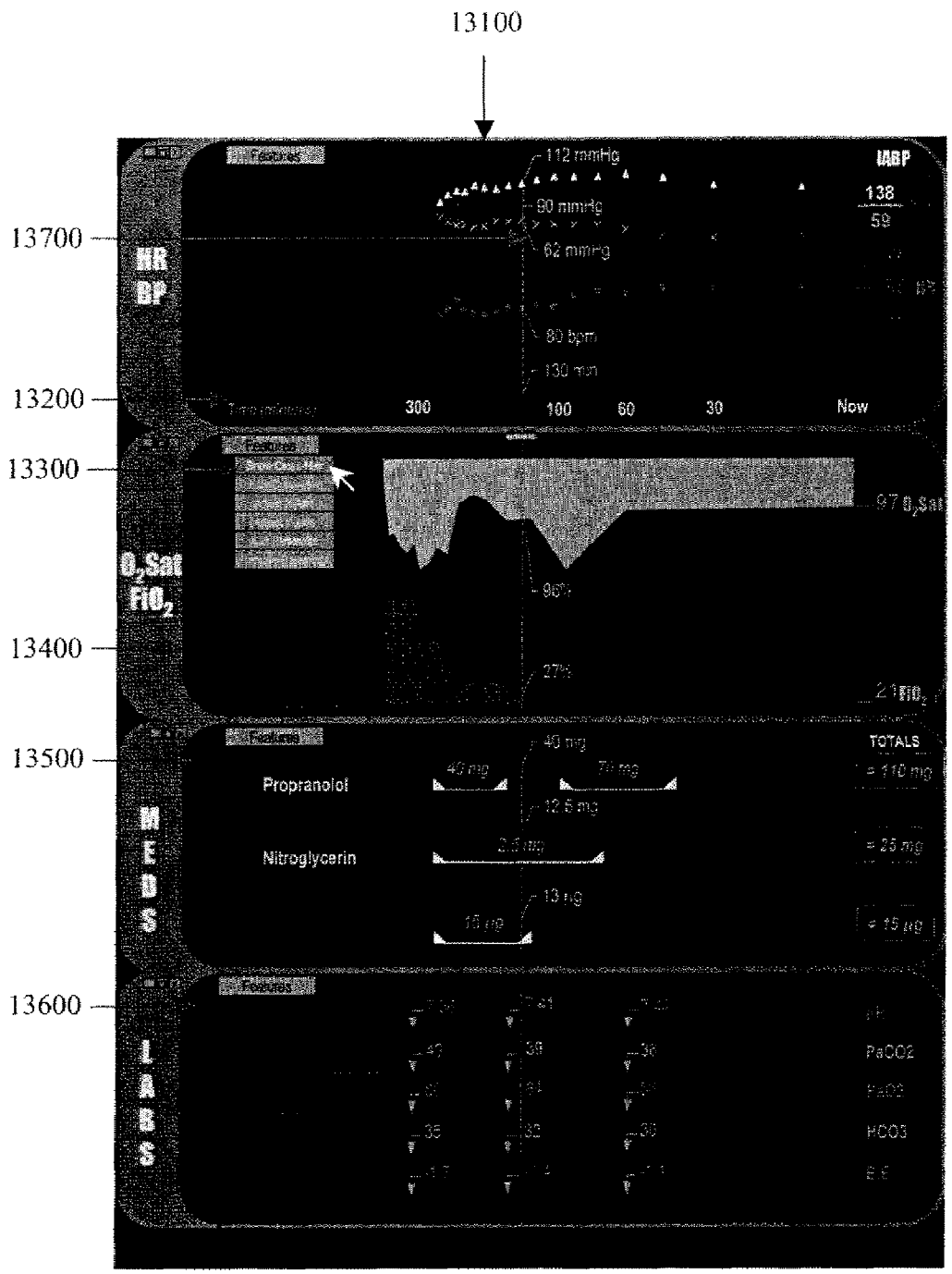
FIG. 13 is an exemplary user interface element illustrating an invocation of a cross hairs feature via a features menu 13300.
Figure 14:
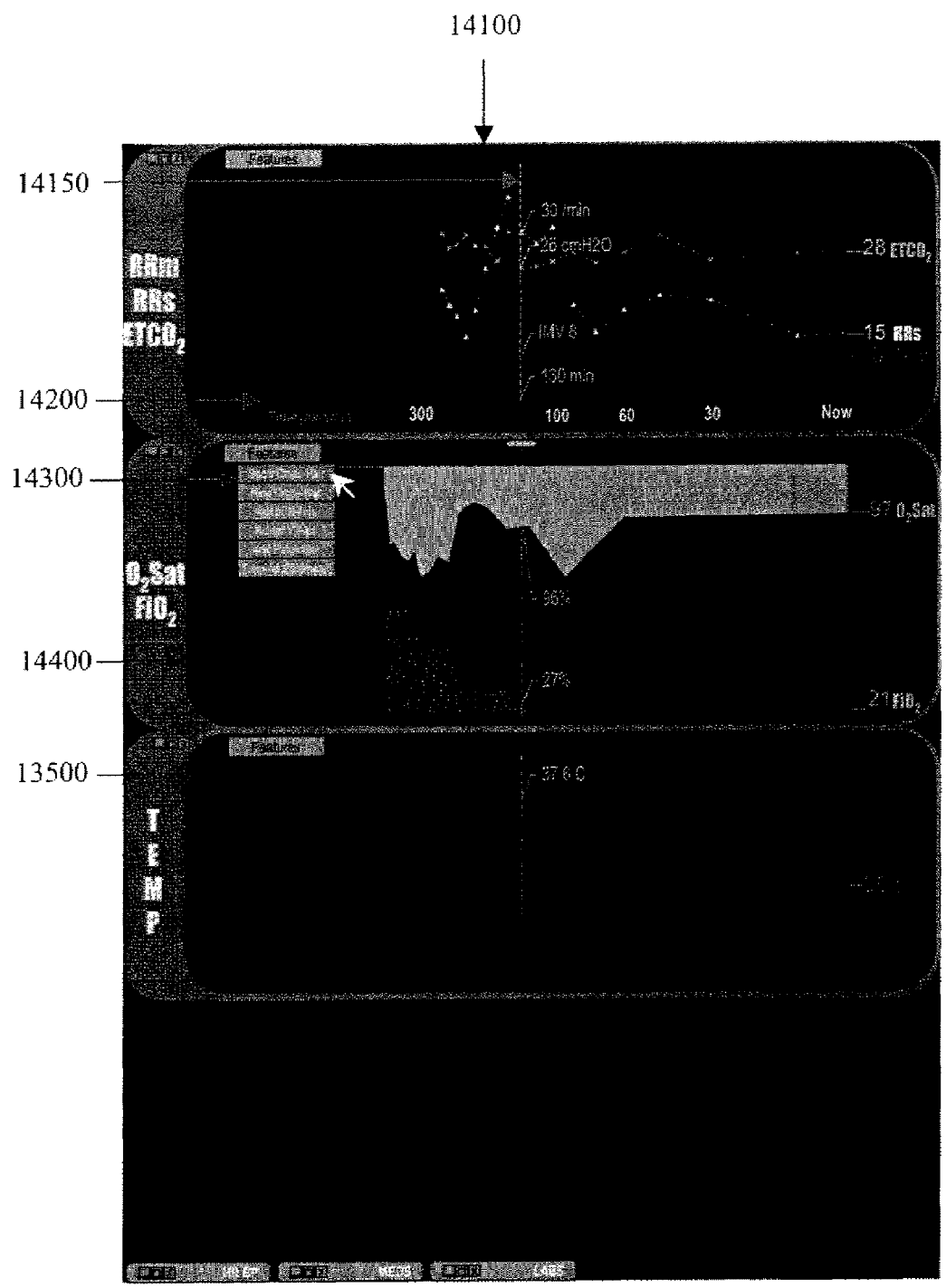
FIG. 14 is an exemplary user interface element illustrating a compressed plot time interval for a set of plots in which data are compressed to the left of a cross hair 14150.
Figure 15:
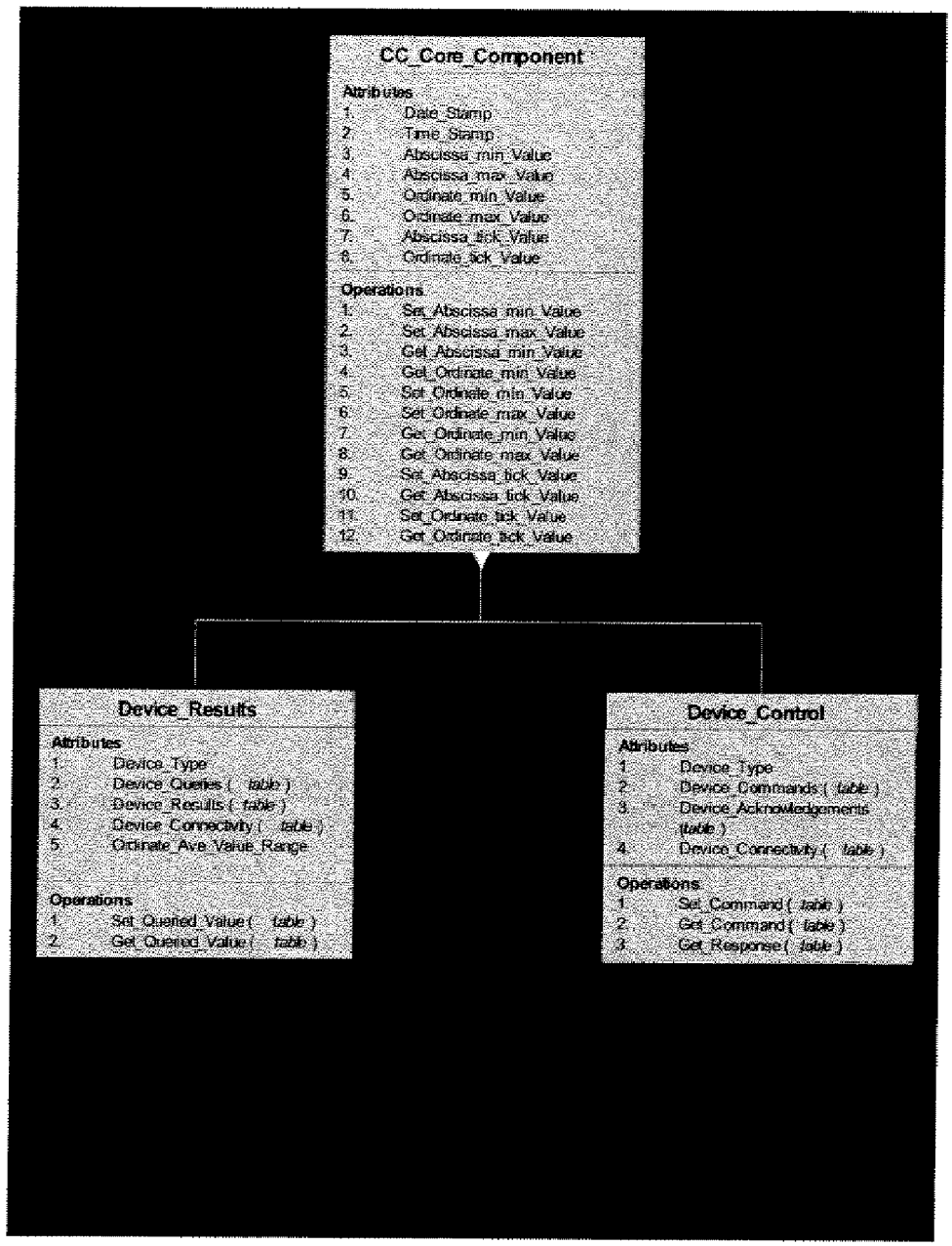
FIG. 15 is an exemplary user interface illustrating pseudocode for an object oriented data model.

FIGS. 2-10 show how the components are assembled using the principals of object-oriented programming. FIGS. 11-14 show the resulting display and automatic time synchronization. In particular, FIG. 13 shows the synchronization of the time-intervals with the shared "cross hair", such as cross hair 11600 of FIG. 11, over each component. FIG. 14 shows how the compressing the interval also synchronizes each display allowing clinicians to quickly reconfigure the display to investigate the clinical question they are trying to answer as they look at the display. FIG. 15 shows representative underlying code and object-oriented functionality that supports the attributes of the system.

Figure 3:
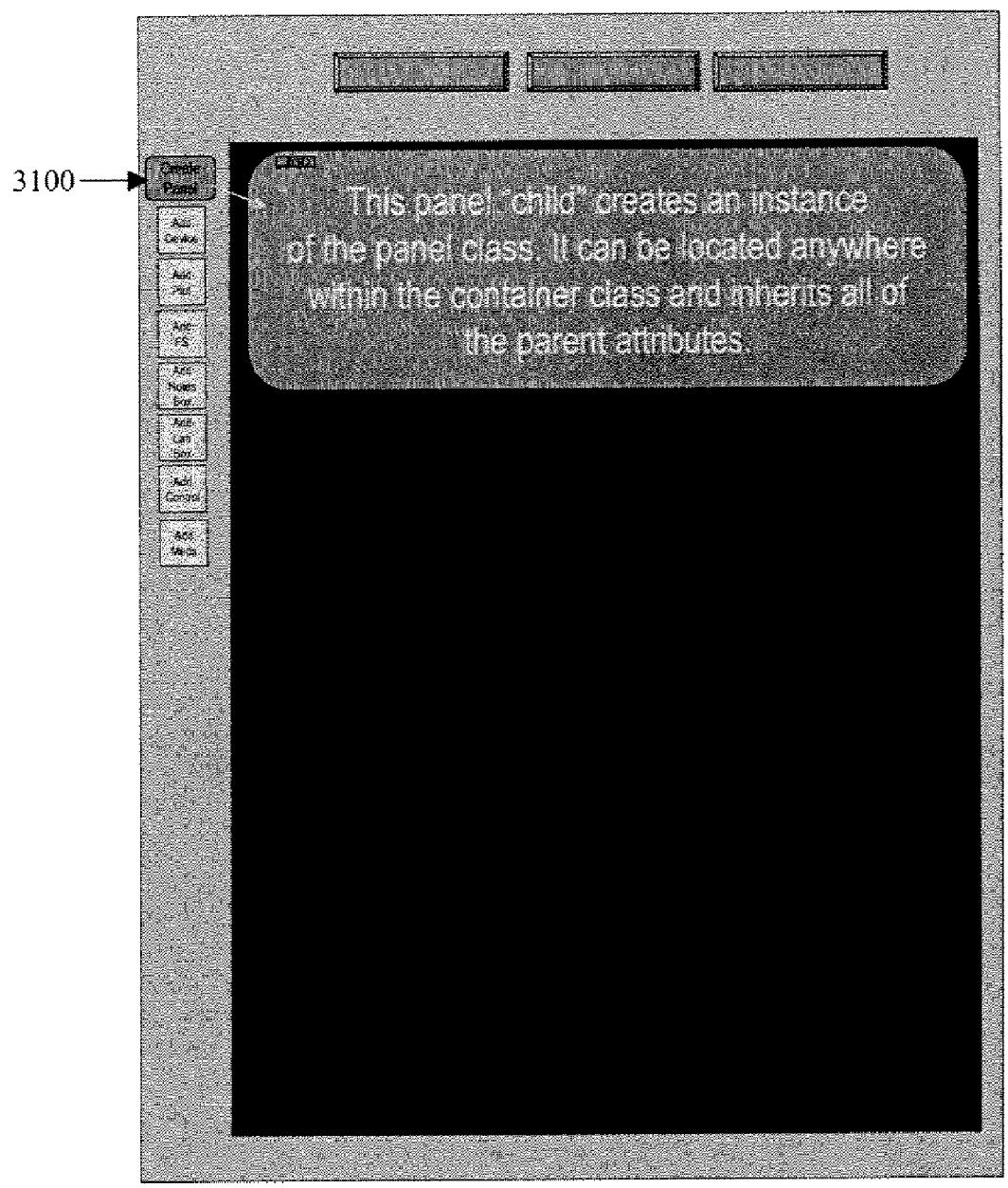
FIG. 3 is an exemplary user interface element regarding use of a Create panel icon.

FIG. 3 is an exemplary user interface element regarding use of a Create panel icon 3100). When a user selects Create panel icon 3100, the system creates a new panel for display via the user interface. The panel is of a child class. The panel inherits attributes and functionality from a container class, and acts as base class for subcomponents. The panel is located in a window and is placeable by the user at a desired location in the window. Adding a device and/or connecting a patient to a medical device causes an automatic update of the panel and/or user interface, or at least a message to the user that the new device is available.

Figure 4:
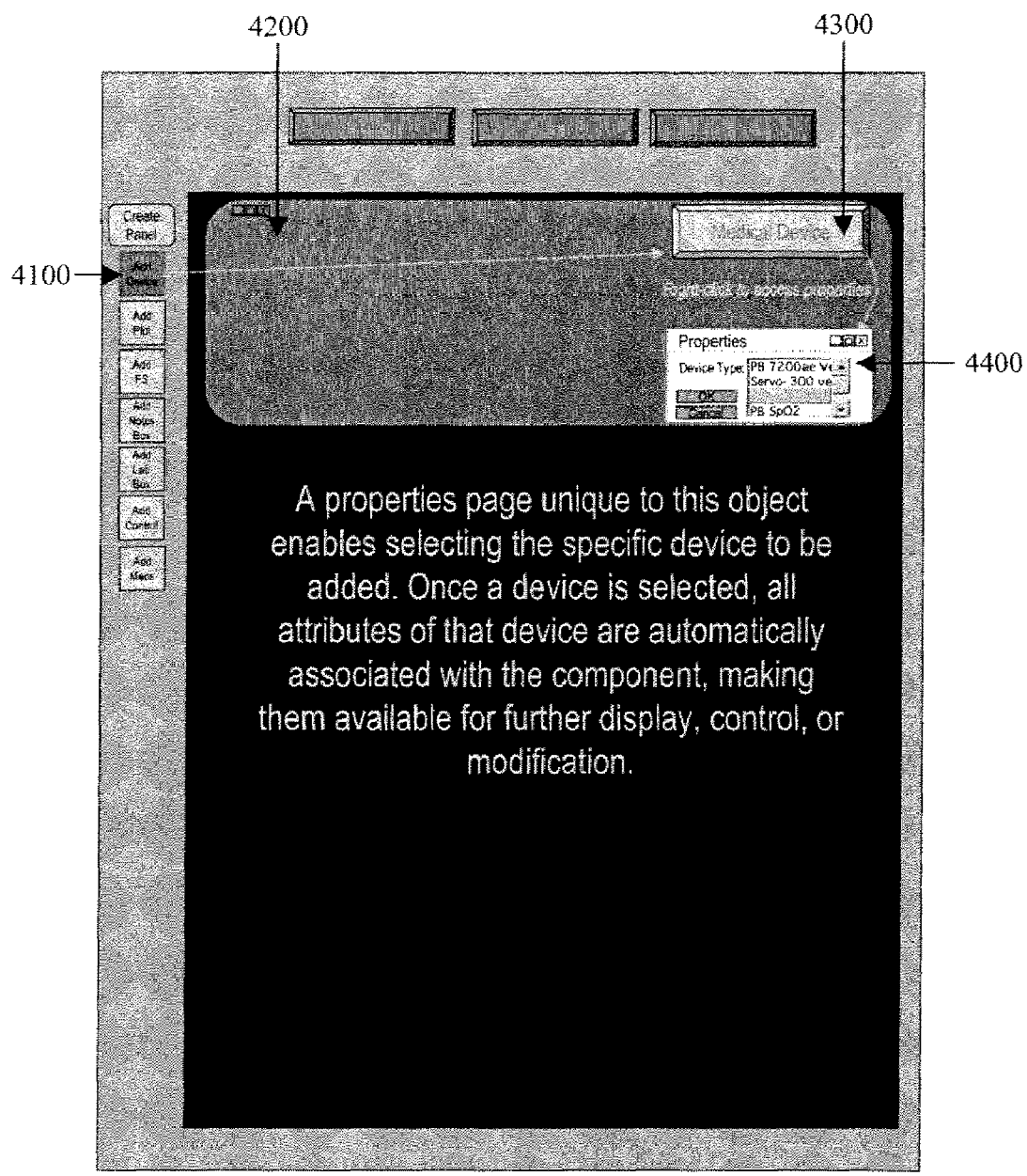
FIG. 4 is an exemplary user interface element regarding use of an Add device icon 4100.

FIG. 4 is an exemplary user interface element regarding use of an Add device icon 4100. Invoking Add device icon 4100 causes a display of an image window 4200, which comprises a medical device icon 4300. When a user selects Medical device icon 4300, the system creates a properties image window 4400. Properties image window 4400 is adapted for the user to select a device type of a desired device. Device properties selection establishes parameters and functions that are employed with a selected object and assists in rendering one or more display panels related to the device, each of which can display in accordance with the selected device properties.

Figure 5:
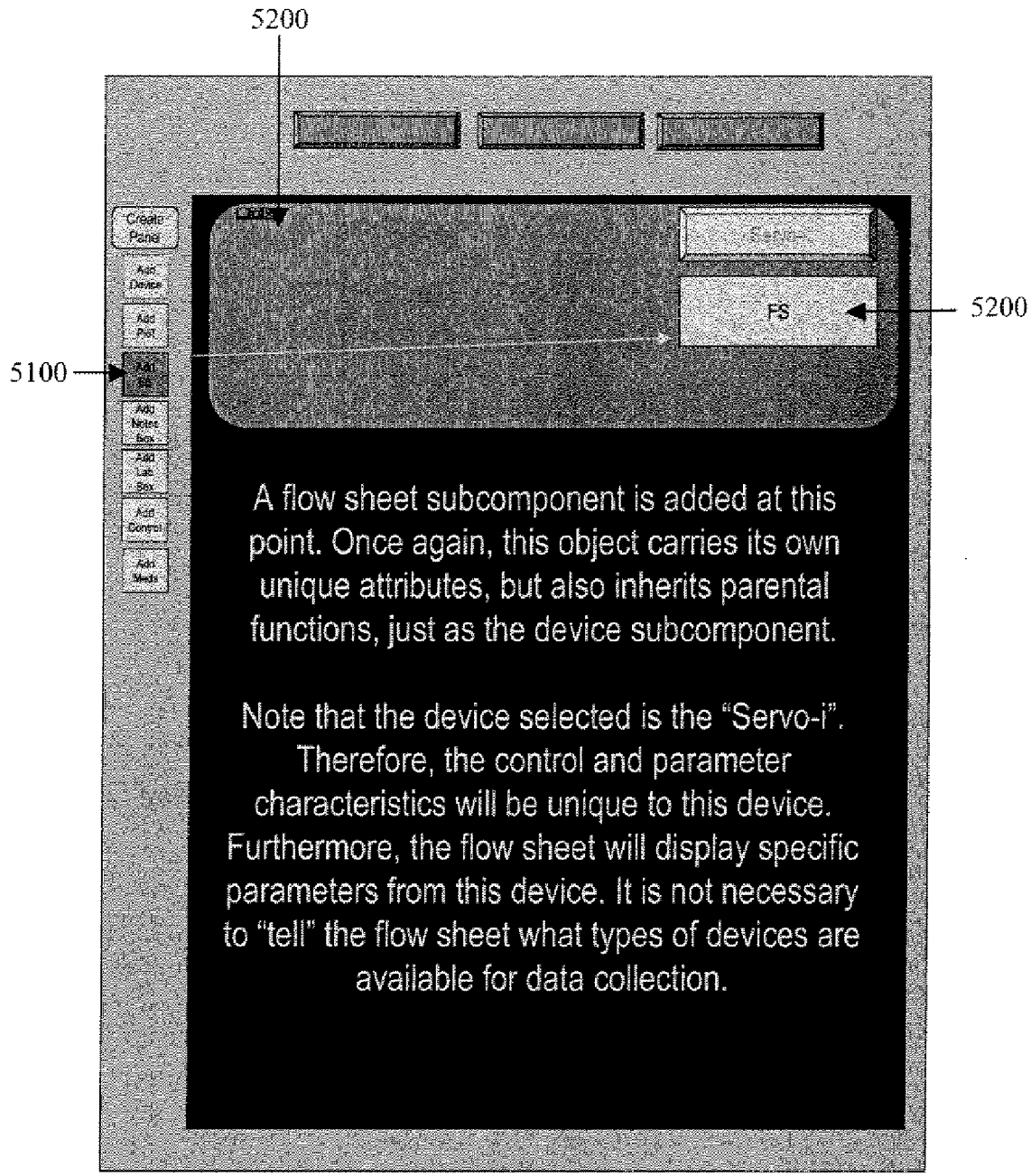
FIG. 5 is an exemplary user interface element regarding use of an Add flowsheet icon 5100.

FIG. 5 is an exemplary user interface element regarding use of an Add flowsheet icon 5100. A user selects Add flowsheet icon 5100 resulting in a display of a panel 5200, which comprises a Flowsheet properties icon 5300 for an exemplary device denoted as "Servo-i". A flow sheet component is added to panel 5200 to provide a text-based window to view data collected from devices. Flowsheets created via Add flowsheet icon 5100 each have unique attributes, but also can inherit attributes.

Figure 6:
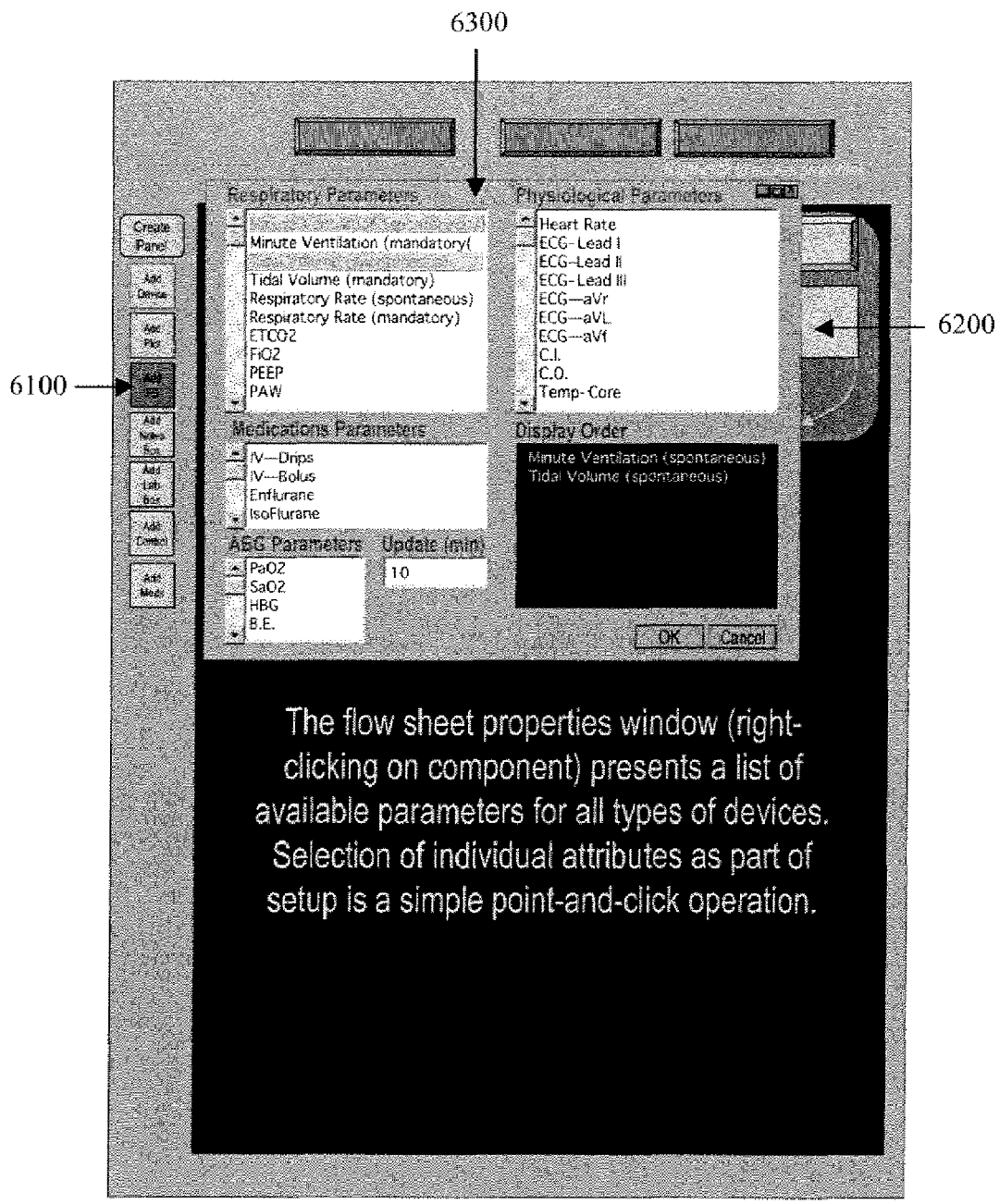
FIG. 6 is an exemplary user interface element regarding use of a Add flowsheet icon 6100.

FIG. 6 is an exemplary user interface element regarding use of an Add flowsheet icon 6100. When a Flowsheet properties icon 6200 is selected, activated, and/or invoked, a panel 6300 is rendered, which is adapted for a user to select individual parameter attributes for display within the flow sheet display window. These individual parameters are in addition to any provided by the parent environment. In this particular embodiment, the parameters comprise respiratory parameters, physiological parameters, medications parameters, arterial blood parameters, an update frequency, and/or a display order. Panel 6300 also provides control buttons to select highlighted parameters or to cancel entries of panel 6300.

Figure 7:
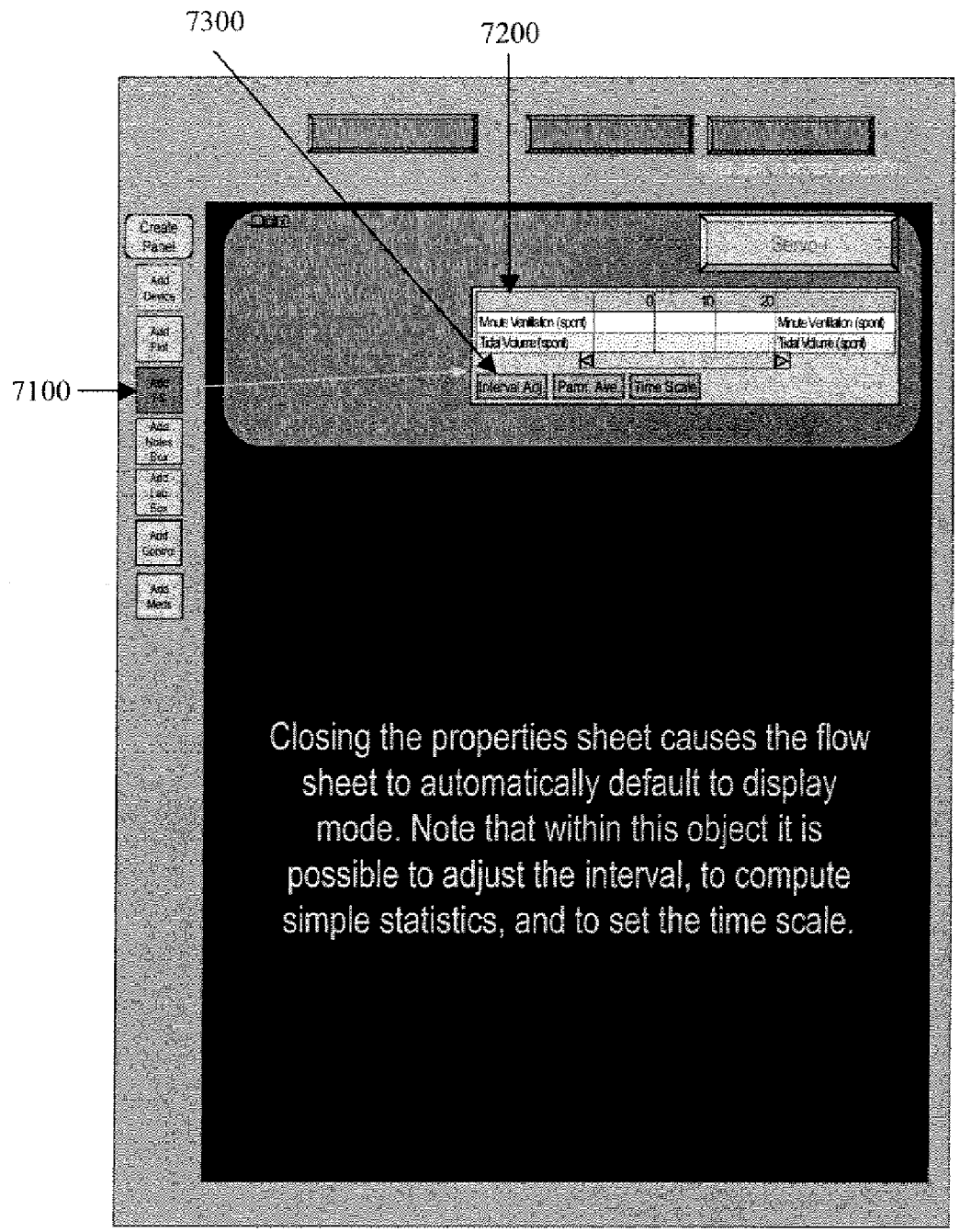
FIG. 7 is an exemplary user interface element that comprises an exemplary flowsheet 7200.

FIG. 7 is an exemplary user interface element that comprises an exemplary flowsheet 7200, which is rendered responsive to a user invocation of Add flowsheet icon 7100. Flowsheet 7200 is displayed responsive to parameter attributes selected via a user interface such as the user interface illustrated in FIG. 6. Flowsheet 7200 is adapted for accepting a user selection for changing flowsheet 7200. For example, double-clicking on an axis of flowsheet 7200 launches the property window for that axis. Adjusting a time range for flowsheet 7200 is done through an adjustment window and accessed through an Interval adjustment icon 7300.

Figure 8:
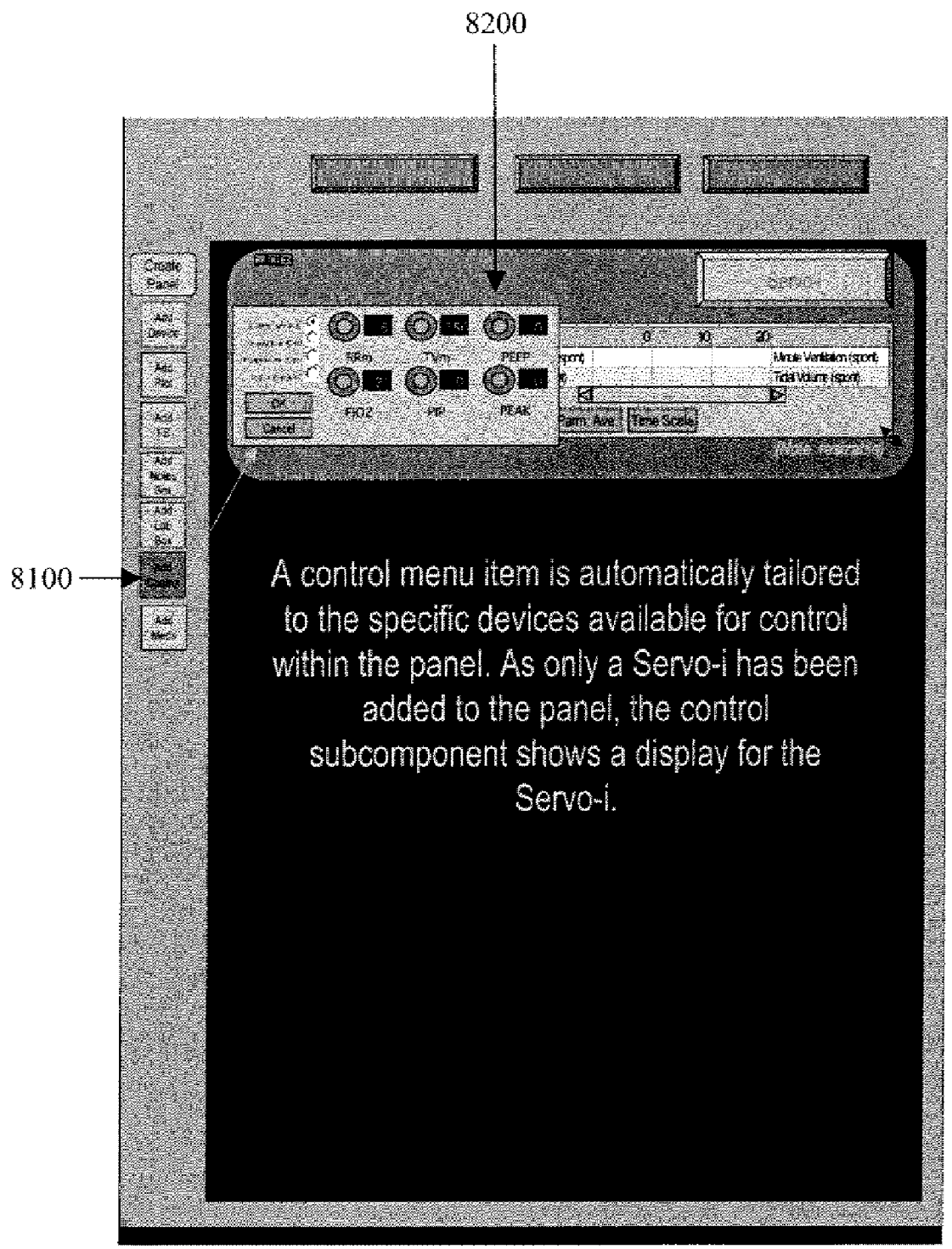
FIG. 8 is an exemplary user interface element regarding use of an Add control icon 8100.

FIG. 8 is an exemplary user interface element regarding use of an Add control icon 8100. A user selection of Add control icon 8100 causes a display of panel 8200 which displays information related to a predetermined medical device, such as the device denoted as "Servo-i" in the illustrated embodiment. One or more device control subcomponents are added as needed based upon a number of devices available. The device control subcomponents provide for the remote control of devices at the user interface, which can be at a point of care.

Figure 9:
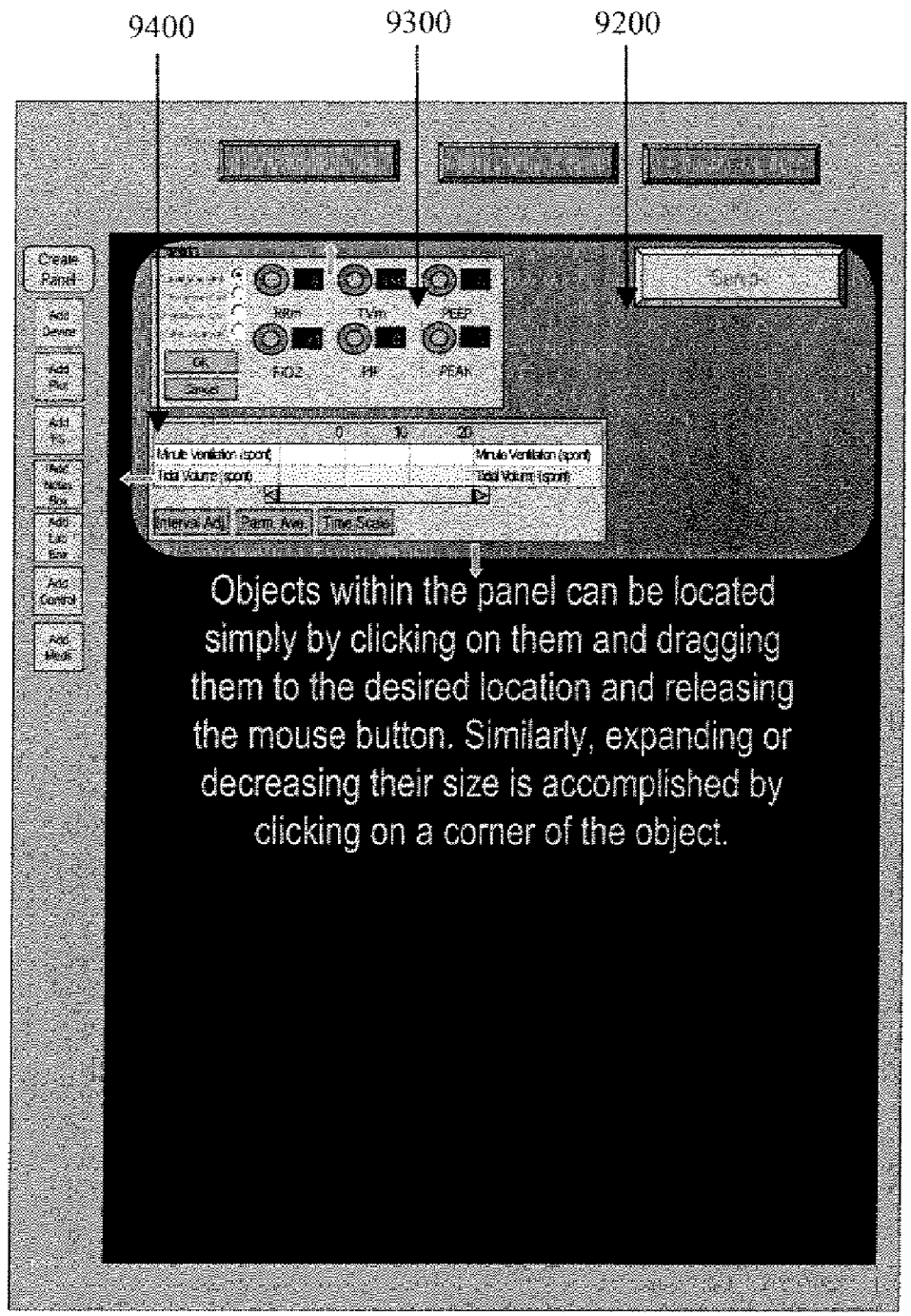
FIG. 9 is an exemplary user interface element.

FIG. 9 is an exemplary user interface element, which comprises a first panel 9200. First panel 9200 comprises a second panel 9300 and a third panel 9400. A user, via a pointing device (e.g., a mouse, trackball, touchpad, joystick, etc,), can move second panel 9300 and/or third panel 9400 to a desired location within first panel 9200. A user can adjust a size of second panel 9300 and/or third panel 9400 by clicking on a predetermined object corner of second panel 9300 and/or third panel 9400 respectively.

Figure 10:
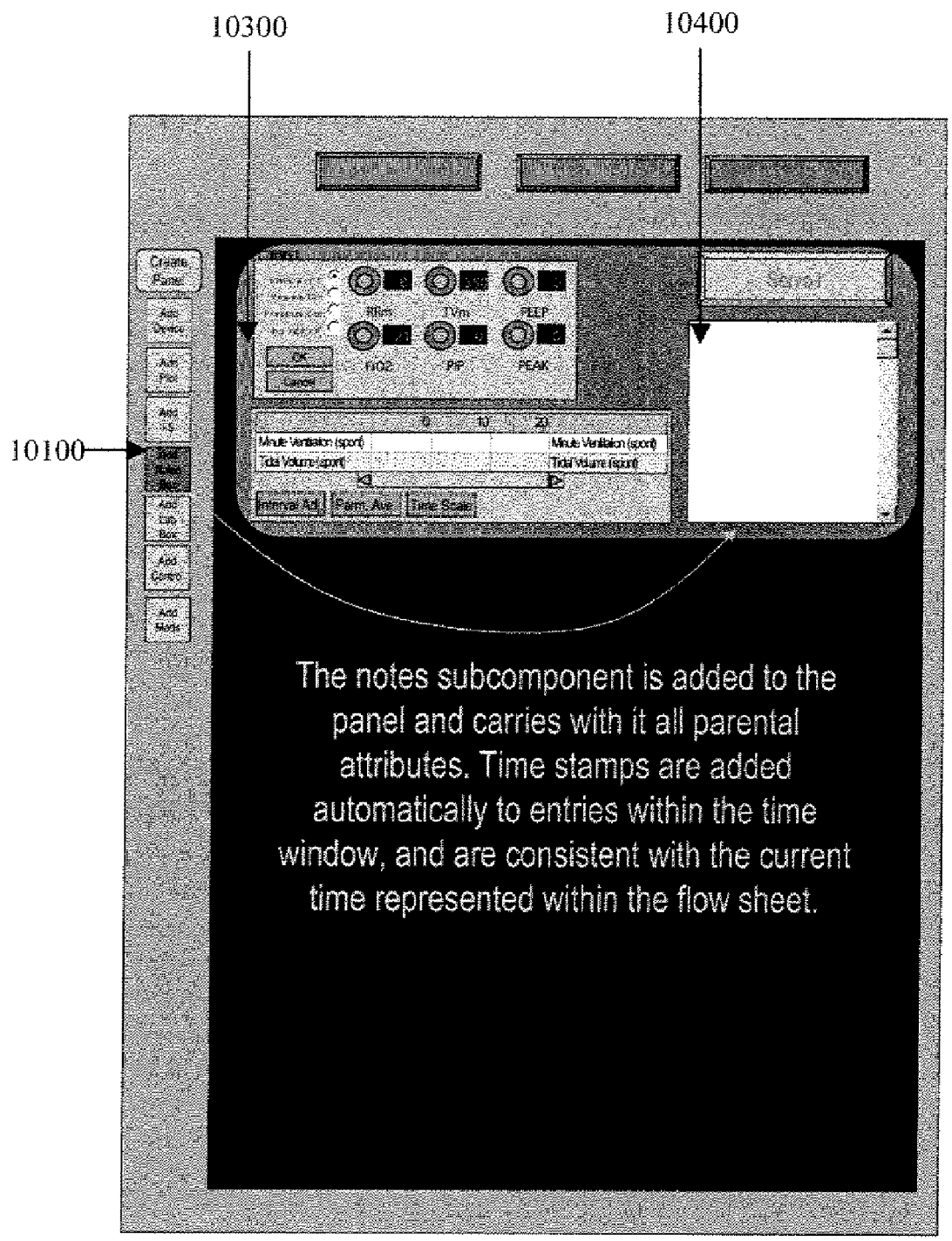
FIG. 10 is an exemplary user interface element regarding use of an Add notes icon 10100.

FIG. 10 is an exemplary user interface element regarding use of an Add notes icon 10100. When a user selects Add notes icon 10100, a user notes panel 10400 is created in panel 10300. Notes panel 10400 captures user-entered text. The system automatically determines a time at which the user enters the user text and automatically time stamps the text (that is, upon entering text, a time and date stamp is automatically inserted above and/or in a predefined location with respect to the text).

Figure 11:
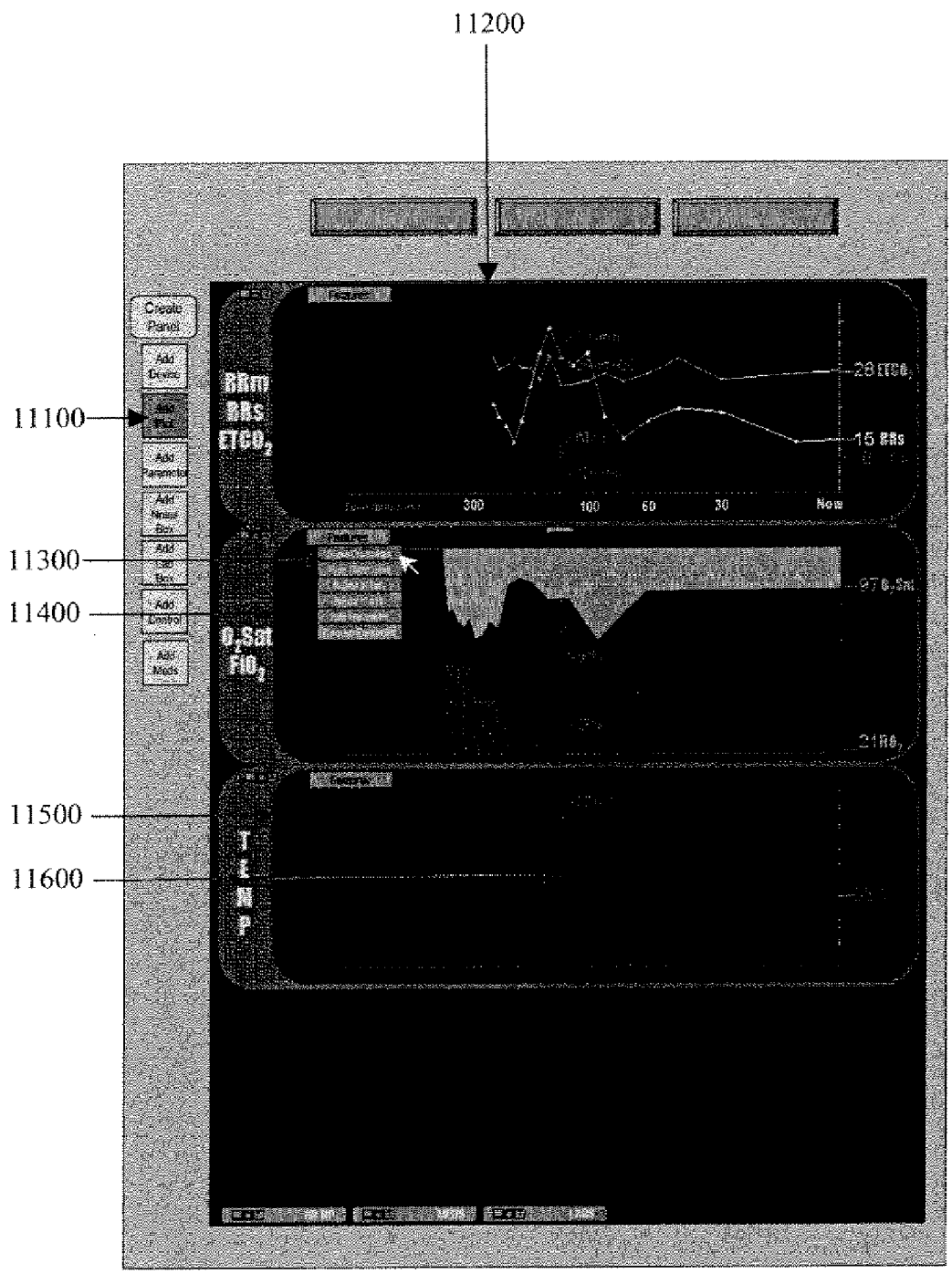
FIG. 11 is an exemplary user interface element regarding use of an Add plot icon 11100.

FIG. 11 is an exemplary user interface element regarding use of an Add plot icon 10100. When a user selects Add plot icon 10100, the system is adapted to add a plot to a rendered window. For example, the window of FIG. 11 comprises a first panel 11200, a second panel 11400, and a third panel 11500. First panel 11200 comprises plotted data related to respiratory parameters of a patient. Second panel 11400 comprises information related to blood oxygen content. Third panel 1150 comprises a plot of a body temperature of the patient. Each of first panel 11200, second panel 11400, and third panel 11500 comprises a single independent time axis along and/or with respect to which data is plotted. The time axis is divided via a cross hair 11600). The time axis divider can indicate a change in a tithe scale from a relatively compressed time scale (such as left of cross hair 11600 and a relatively uncompressed time scale (such as right of time cross hair 11600). In an alternative embodiment, each panel can comprise its own time axis, although each such time axis is substantially similar in scales, division among scales, units, alignment of specific times, etc. with each other time axis of that window.

Each of first panel 11200, second panel 11400, and third panel 11500 comprises a features icon, such as features icon 11300 of second panel 11400. Via features icon 11300, a user can show or hide cross hair 11600, adjust the abscissa of second panel 11400, adjust an ordinate axis of second panel 11400, add a parameter to second panel 11400, and/or remove a parameter from second panel 11400. An additional panel can be added to FIG. 11, via the user selection of Add plot icon 11100. For example, a separate panel might be added below third panel 11500. Added panels inherit parental attributes and functions. Monitored patient data is shown within the same plot window.

Figure 12:
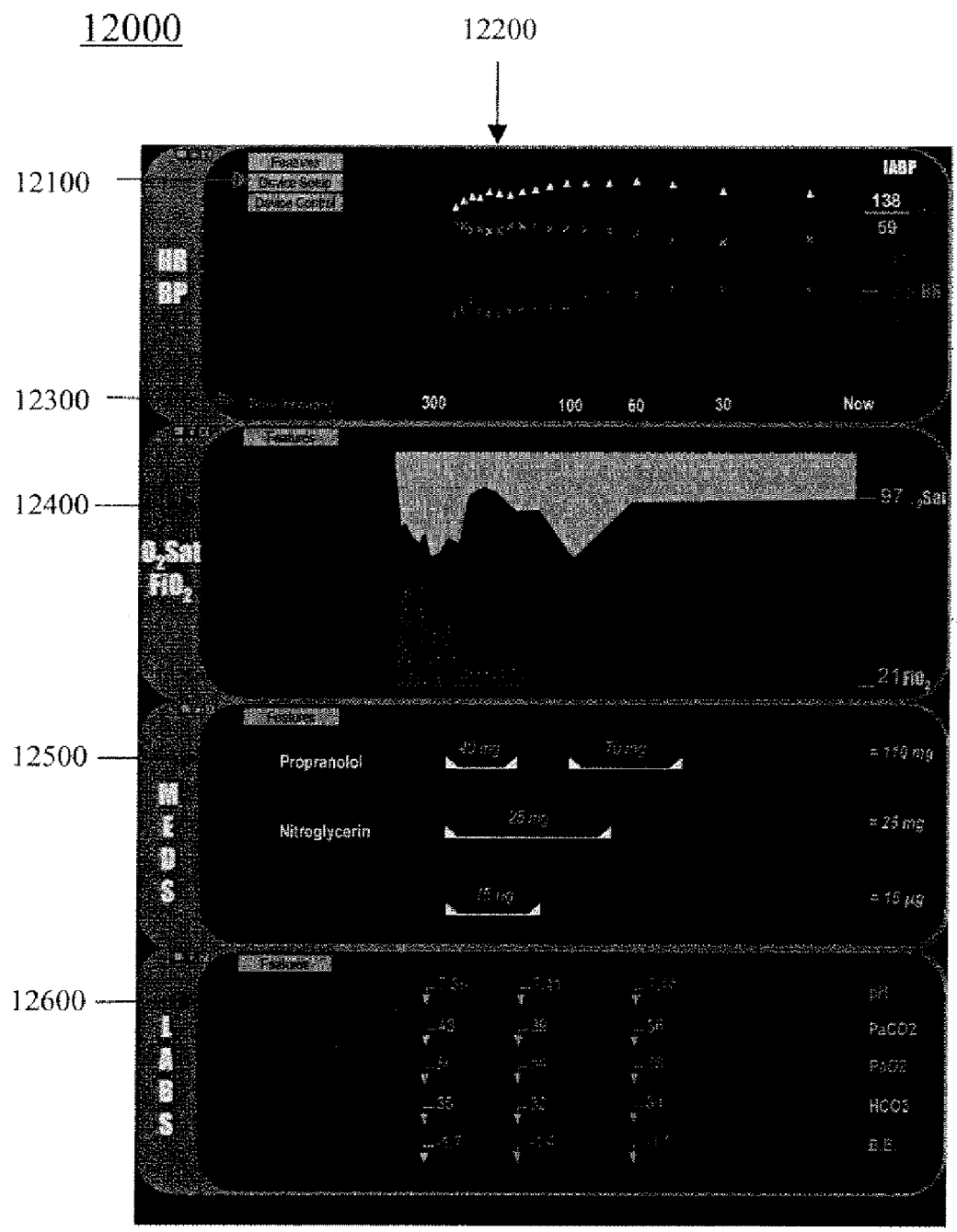
FIG. 12 is an exemplary fully populated panel 12000.

FIG. 12 is an exemplary fully populated panel 12000, which comprises: a first panel 12200 showing a heart rate and blood pressure of a patient; a second panel 12400 showing blood chemistry plots of the patient; a third panel 12500 showing medicament dosage to the patient; and a fourth panel 12600, showing lab results for a patent.

An illustrated time axis 12300 for panel 12000 is common for first panel 12200, second panel 12400, third panel 12500, and fourth panel 12600. Each of first panel 12200, second panel 1240(, third panel 12500, and fourth panel 12600 comprises a features icon, such as features icon 12100 of first panel 12200. Features icon 12100 is adapted for a user to setup and/or control a device associated with features icon 12100. For example, a user might provide information to the system related to a pulse monitor and/or adjust a sampling frequency for obtaining measured values of the patient from the pulse monitor.

FIG. 13 is an exemplary user interface element illustrating an invocation of a cross hairs feature via a features menu 13300. The user interface element comprises a first panel 13100, second panel 13400, third panel 13500, and fourth panel 13600. The selection by the user of showing cross hairs via features menu 13300 can invoke an object, which can change one or more features of a parent container class for first panel 13100, second panel 13400, third panel 13500, and/or fourth panel 13600. Plotted time-based data comprise a common time axis 13200, and overlaying a cross hair 13700 (depressing a control button on the keyboard) allows user to manually slide cross hair 13700 over a single plot and see the corresponding changes in sibling plots. The current value of parameters is shown (where applicable) as cross hair 13700 is moved.

FIG. 14 is an exemplary user interface element illustrating a compressed plot time scale for a set of plots in which data are relatively compressed to the left of a cross hair 14150. FIG. 14 comprises a first panel 14100, second panel 14400, and third panel 14500. Cross hair 14150 is invoked and placed in first panel 14100 via a features icon 14300 comprised by second panel 14400. The plots to the right of cross hair 14150 are relatively uncompressed. Compressing plotted data allows for data collected over a longer time period to be shown within a field of view of a respective panel. Other panels can be minimized, as illustrated in the lower left-hand corner of the container window, so that instead of using separate container windows the plots can be minimized out of the way when not needed. The plots are visible immediately upon clicking on the maximize feature of the iconic bar displays.

FIG. 15 is an exemplary user interface illustrating pseudocode for an object oriented data model. This pseudocode is adapted to create a user interface wherein results and device controls are inherited from a parent class that enables plotting, query control, and/or visualization etc.

Certain exemplary embodiments comprise features such as flow sheets and Intensive Care Unit (ICU) display technologies that comprise:

An object-oriented graphical display structure whereby components for data display and device control are overlaid and applied as subcomponents of the container window into which they are assembled. In this process they automatically inherit attributes and functionality of the parent container class while maintaining the ability to integrate their own object attributes. The object inheritance process enables the children (objects placed on the container) to acquire the attributes of their parents while at the same time they can possess unique characteristics (such as controls) that are distinct from other "children".

In this way, a child object associated with a ventilator controller (Example: a connected Servo-i) inherits from the parent container the time-axis attributes, the scale, the actual location on the display, colors, symbols, etc. while still displaying the default inherent-to-the-device values of: tidal volume, respiratory rate, inspiratory concentration of oxygen, pressures, and/or flows, etc.).

As devices are selected, the added panels, device control, and device display subcomponents automatically reflect the associated devices, without requiring manual selection.

Information is displayed to the user in a container-based view whereby timeline is linked and the ability to select a single parameter and show the state of other parameters is done using a single click (that is, selection of a single parameter).

The display allows for the adding and deleting of subcomponents via simple operations such as drag, drop, and/or delete, etc. Movement and location of subcomponents within display panels and display panels within containers is accomplished in a "What You See Is What You Get" (WYSIWYG) display format.

The system is usable in a variety of applications including in the operating room environment: anesthesia related products, monitors, and/or information systems, post anesthesia care units and/or recover rooms: and in the emergency department monitors and/or information systems; etc.

System features are those base attributes and methods (functions) that are made available to the parental container. These are established at a design phase of exemplary embodiments and comprise:

object-based display integration, in which classes share a common container and panel, and thereby inherit features therefrom;

automated display integration of an arbitrary number of concurrently controllable display formats for various devices;

automated integration into this environment of concurrently controllable clinician data entry tools, specifically documentation and orders;

automated integration into this environment of multiple modes of concurrently controllable documentation specifically narrative text and flow sheet documentation;

computational format that allows automated concurrently controllable integration of two-way device interaction—not only output displays but also device settings such as for mechanical ventilators and intravenous (IV) fluid delivery pumps;

automatic concurrently controllable integration between devices and the multiple different display modalities;

allows automated time coordination over time between multiple different display formats (e.g. single time line slices for spreadsheet type data, monitored patient data, graphical-type data as well as simultaneous compressed versions of these formats);

supports consistent display formats on multiple different end-users devices.

packages these services as API with object-oriented programming tools; and/or package these services as API with XML/SOAP industry standards; etc.

The system provides an in-room display device for clinical environments where multiple machine generated real-time data streams are needed to provide care. Such settings include operating rooms; recovery rooms; emergency rooms; and/or any type of cardiac, respiratory, neurosurgical, neonatal, pediatric, and/or post surgical critical care units.

The following text, written in a "pseudocode format" illustrates implementation of an exemplary user interface structure. The example includes a container class, an abstract base class and two sample component classes. The pseudocode illustrates the structure without providing the specific code details (for clarity purposes) for compilation or interpretation on a specific computer (in this case using selected Java programming language notation). The example is described as software objects with encapsulated software methods and data fields. A selected subset of potential sample methods and data fields is shown for illustrative purposes.

The top level display environment can be partially described in pseudocode as:

```
Public class DisplayEnvironment {
int DisplayPixelHeight;
int DisplayPixelWidth;
int MaximumNumberComponentSlots;
char TimeScaleCompression;
PatientDemographics specificPatientDemographics;
public void AddCCComponent {...} /* invokes new component of the class CCComponent
public void RemoveCCComponent {...}
public void ReorderCCComponent {...}
public void ResizeCCComponent {...}
public void SetTimeCCCompression {...}
public void GetTimeCCCompression {...}
};
```

The components are described using a CriticalCare ("CC") base class. An individual component implements both features described in the base class as well as component specific features. The tree of display components is invoked by the Display Environment class or program and includes components describing tools such as lab flowsheets, input/output flowsheets, monitored patient data, pulse oximetry, capnometry, narrative notes, and assessments. By using an object-oriented abstract base class, which serves an enforced template. An abstract base class is one that is designed only as a parent class and from which child classes may be derived, and which is not itself suitable for instantiation. In this way the system can synchronize the entire set of object-based component behaviors (that is, methods or functional capabilities) using tools in the DisplayEnvironment or a similar user interface control class. In particular, functions such as the DisplayEnvironment:ReordeCCComponent and the DisplayEnvironment:ResizeCCComponent methods specifically illustrate the instantiation of the system. These classes enable the user to reorder components within the interface, or to resize the user interface while retaining the relative position of objects within the base container. Again, the pseudocode examples below illustrate a subset of possible fields and methods to illustrate the system. Actual code would have more fields and methods.

```
Abstract public class CCComponent {
char TimeCursor;
char DataFeedIPAddress;
char CCComponentLabel;
char CCComponentHeaderText;
public void InvokeComponent ( )
public void ResizeComponent ( )
public void SetNumericComponentParameters ( )
public void SetTextParameters ( )
public void SetTimeCursorSynchronization ( )
}
```

The above base class serves as the parent for the specific controlled modules. Examples of selected pseudocode for components display patient fluid input and outputs as well as patient data obtained via monitors are described below. These components use the centralized time coordination and display controls of the system and automatically combine these with specific device and software component features. In contrast, without use of the system, this code might have to be written in duplicate and it might be relatively difficult for a software developer or a user to easily control all of the components simultaneously.

```
public Class Input/OutputComponent extends CCComponent {
/* implements each of the methods and fields in the base class as well
as the following methods and fields specific in patient fluid inputs and
outputs */
GridControl I&OGridControl;
GridControlText I&OGridControlText;
GridControlNumerics I&OGridControlNumerics;
public void InitializeI&OGrid {...}
public void CalculateI&OGrid {...}
public void InitializeI&OGridAlerts {...}
public void InitializeI&OTimeCursor {...}
public void AddNewIVDeviceI&O {...}
public void RemoveNewIVDeviceI&O {...}
}
public Class TelemetryComponent extends CCComponent {
/* implements each of the methods and fields in the base class as well
as the following methods and fields specific to cardiac rhythm
monitoring */
TelemetryControl TelemetryControl;
TelemetryControlLabels TelemetryControlLabels;
TelemetryControlHeight TelemetryControlHeight;
public void InitializeTelemetry {...}
public void InitializeTelemetryArrhythmiaAlarms {...}
public void SetTelemetryArrhythmiaAlarms {...}
public void InitializeTimeCursor {...}
public void DisplayTelemetryLeadsData {...}
}
```

Still other practical and useful embodiments will become readily apparent to those skilled in this art from reading the above-recited detailed description and drawings of certain exemplary embodiments It should be understood that numerous variations, modifications, and additional embodiments are possible, and accordingly, all such variations, modifications, and embodiments are to be regarded as being within the spirit and scope of this application.

What is claimed is:

1. A system, comprising:
   a patient medical parameter processor adapted for,
      automatically acquiring data representing a plurality of different types of medical parameters of a patient and processing said data for presentation to a user via a display device and
      using the acquired medical parameters to detect a change in patient status and automatically initiating adding or removing an image window displaying a medical parameter in response to the detected change in patient status; and
   a display processor adapted for initiating display of:
      a plurality of different image windows presenting processed data representing and corresponding to said plurality of different types of medical parameters of said patient on said display device, each of said plurality of different image windows referenced to a single variable scale timeline comprising different consecutive time scales and arranged on said display device to permit said user to view values for each of said plurality of different types of medical parameters corresponding to a substantially common time from said single variable scale timeline; and
      a plurality of user interface elements implemented using object oriented executable code, each of said plurality of user interface elements adapted to provide a user selectable single setting of image display format characteristics shared by said plurality of image windows.

2. A system according to claim 1, wherein
said patient medical parameter processor, in response to detecting plug-in of an additional patient monitoring device, automatically initiates adding an image window displaying a medical parameter acquired by said additional patient monitoring device.

3. A system according to claim 1, wherein said patient medical parameter processor, automatically initiates archiving medical parameter data of a patient associated with a removed image window in response to the detected change in patient status.

4. A system according to claim 1, wherein
said single variable scale timeline comprises time scale selected from a logarithmic time scale, semi-logarithmic scale, and exponential time scale,
said single variable scale timeline comprises a first time period having a first time scale and a second time period having a second time scale, said first time scale differing from said second time scale, and
said first time scale is presented together with data representing compressed medical parameter data of said patient, said compressed medical parameter data comprising a reduced number of data points.

5. A system according to claim 1, wherein
said single variable scale timeline comprises a first time period having a first time scale and a second time period having a second time scale, said first time scale differing from said second time scale,
said first time scale is presented together with data representing compressed medical parameter data of said patient, said compressed medical parameter data comprising a reduced number of data points, and
said reduced number of data points is derived from amalgamated data points.

6. A system according to claim 1, wherein
said plurality of image windows are derived using a corresponding plurality of object-oriented programming objects sharing common core attributes and inheriting attributes from parent classes.

7. A system according to claim 1, wherein
said plurality of user interface elements comprises a cross hair adapted to show said values for each of said plurality of different types of medical parameters of said patient, each of said values corresponding to said substantially common time from said single variable scale timeline.

8. A system according to claim 1, wherein
said patient medical parameter processor, in response to detecting plug-in of an additional patient monitoring device, automatically receives parameterized control settings and transfers the settings to an image window displaying a medical parameter acquired by said additional patient monitoring device and
said user selectable single setting is a time value.

9. A system according to claim 1, wherein
said plurality of user interface elements comprises a documentation tool adapted to receive entry of at least textual notes.

10. A system according to claim 1, wherein
said plurality of user interface elements is dependent on a role of the user.

11. A method implemented by at least one processing device executing machine readable instructions, comprising the steps of:
automatically acquiring data representing a plurality of different types of medical parameters of a patient and processing said data for presentation to a user via a display device;
using the acquired medical parameters to detect a change in patient status and automatically initiating adding or removing an image window displaying a medical parameter in response to the detected change in patient status; and
initiating display of:
a plurality of different image windows presenting processed data representing and corresponding to said plurality of different types of medical parameters of said patient on said display device, each of said plurality of different image windows referenced to a single variable scale timeline comprising different consecutive time scales and arranged on said display device to permit said user to view values for each of said plurality of different types of medical parameters corresponding to a substantially common time from said single variable scale timeline; and
a plurality of user interface elements implemented using object oriented executable code, each of said plurality of user interface elements adapted to provide a user selectable single setting of image display format characteristics shared by said plurality of image windows.

12. A method according to claim 11, wherein
said patient medical parameter processor, automatically initiates archiving medical parameter data of a patient associated with a removed image window in response to the detected change in patient status.

13. A method according to claim 11, wherein
said single variable scale timeline comprises a first time period having a first time scale and a second time period having a second time scale, said first time scale differing from said second tune scale, and
said first time scale is presented together with data representing compressed medical parameter data of said patient, said compressed medical parameter data comprising a reduced number of data points.

14. A method according to claim 11, wherein
said single variable scale timeline comprises a first time period having a first time scale and a second time period having a second time scale, said first time scale differing from said second time scale,
said first time scale is presented together with data representing compressed medical parameter data of said patient, said compressed medical parameter data comprising a reduced number of data points, and
said reduced number of data points is derived from amalgamated data points.

15. A method according to claim 11, wherein
said plurality of image windows are derived using a corresponding plurality of object-oriented programming objects sharing common core attributes and inheriting attributes from parent classes.

16. A method according to claim 11, wherein
said plurality of user interface elements comprises a cross hair adapted to show said values for each of said plurality of different types of medical parameters of said patient, each of said values corresponding to if said substantially common time from said single variable scale timeline.

17. A method according to claim 11, including the step of in response to detecting plug-in of an additional patient monitoring device, automatically initiates adding an image window displaying a medical parameter acquired by said additional patient monitoring device wherein
said user selectable single setting is a time value.

18. A method according to claim 11, wherein
said plurality of user interface elements comprises a documentation tool adapted to receive entry of at least textual notes.

19. A method according to claim 11, wherein
said plurality of user interface elements is dependent on a role of the user.

20. A machine-readable medium comprising machine instructions executed by a machine and representing activities comprising:
  automatically acquiring data representing a plurality of different types of medical parameters of a patient and processing said data for presentation to a user via a display device;
  using the acquired medical parameters to detect a change in patient status and automatically initiating adding or removing an image window displaying a medical parameter in response to the detected change in patient status; and
  initiating display of:
    a plurality of different image windows presenting processed data representing and corresponding to said plurality of different types of medical parameters of said patient on said display device, each of said plurality of different image windows referenced to a single variable scale timeline comprising different consecutive time scales and arranged on said display device to permit said user to view values for each of said plurality of different types of medical parameters corresponding to a substantially common time from said single variable scale timeline; and
    a plurality of user interface elements implemented using object oriented executable code, each of said plurality of user interface elements adapted to provide a user selectable single setting of image display format characteristics shared by said plurality of image windows.

* * * * *